(12) United States Patent
Brady et al.

(10) Patent No.: US 11,464,528 B2
(45) Date of Patent: Oct. 11, 2022

(54) CLOT RETRIEVAL SYSTEM FOR REMOVING OCCLUSIVE CLOT FROM A BLOOD VESSEL

(71) Applicant: NEURAVI LIMITED, Galway (IE)

(72) Inventors: Eamon Brady, County Galway (IE); David Vale, County Galway (IE); Michael Gilvarry, County Galway (IE); Brendan Casey, County Galway (IE); Marto Hoary, County Galway (IE); Adnan Siddiqui, Williamsville, NY (US)

(73) Assignee: NEURAVI LIMITED, Galway (IE)

( * ) Notice: Subject to any disclaimer, the term of this patent is extended or adjusted under 35 U.S.C. 154(b) by 82 days.

(21) Appl. No.: 16/320,082

(22) PCT Filed: Jul. 25, 2017

(86) PCT No.: PCT/EP2017/068759
§ 371 (c)(1),
(2) Date: Jan. 23, 2019

(87) PCT Pub. No.: WO2018/019829
PCT Pub. Date: Feb. 1, 2018

(65) Prior Publication Data
US 2019/0239910 A1    Aug. 8, 2019

Related U.S. Application Data

(60) Provisional application No. 62/474,383, filed on Mar. 21, 2017.

(30) Foreign Application Priority Data

Jul. 26, 2016 (EP) .................................... 16181338

(51) Int. Cl.
*A61B 17/22* (2006.01)
*A61M 1/00* (2006.01)
*A61B 17/00* (2006.01)

(52) U.S. Cl.
CPC ........ *A61B 17/22012* (2013.01); *A61B 17/22* (2013.01); *A61M 1/743* (2021.05);
(Continued)

(58) Field of Classification Search
CPC .............. A61B 17/22; A61B 17/22004; A61B 17/22012; A61B 2017/22079;
(Continued)

(56) References Cited

U.S. PATENT DOCUMENTS

| 4,445,509 A | 5/1984 | Auth |
| 2005/0054971 A1 * | 3/2005 | Steen .................. A61F 9/00736 604/22 |

(Continued)

FOREIGN PATENT DOCUMENTS

| CA | 2 815 186 C | 12/2015 |
| CN | 1216929 A | 5/1999 |

(Continued)

OTHER PUBLICATIONS

International Search Report and Written Opinion for corresponding International Application No. PCT/EP2017/068759 dated Feb. 1, 2018.

(Continued)

*Primary Examiner* — Darwin P Erezo
*Assistant Examiner* — Christian D Knauss
(74) *Attorney, Agent, or Firm* — Troutman Pepper Hamilton Sanders LLP

(57) ABSTRACT

A system for removing occlusive clot from a blood vessel comprises a catheter and an apparatus for generating a pulsatile vacuum force to pulse the pressure gradient at a (Continued)

distal end of the catheter. The pulse generator may be integral with or separate from the vacuum pump. The pulse generator may be applied to a flexible tubing between the vacuum pump and the proximal end of the catheter.

19 Claims, 18 Drawing Sheets

(52) U.S. Cl.
 CPC ..... *A61M 1/75* (2021.05); *A61B 2017/00141* (2013.01); *A61B 2017/00146* (2013.01); *A61B 2017/00154* (2013.01); *A61B 2217/005* (2013.01)

(58) Field of Classification Search
 CPC .... A61B 2217/005; A61B 2017/00141; A61B 2017/00146; A61B 2017/00154; A61B 17/22032; A61B 2017/2038; A61B 2017/22039; A61B 2017/22067; A61B 2217/007; A61M 1/0037; A61M 1/0035; A61M 1/0009; A61M 1/0056; A61M 1/0062; A61M 1/008; A61M 1/0084; A61M 2025/0078; A61M 2039/2426; A61M 2205/7545; A61M 25/00; A61M 25/007; A61M 25/0075; A61M 25/0082; A61M 39/24; A61M 2202/005; A61M 2202/0413
 See application file for complete search history.

(56) References Cited

U.S. PATENT DOCUMENTS

| | | | |
|---|---|---|---|
| 2005/0192548 A1* | 9/2005 | Dolliver | A61M 1/3696 604/317 |
| 2007/0060888 A1* | 3/2007 | Goff | A61M 25/0068 604/118 |
| 2013/0304003 A1* | 11/2013 | Stiehl | A61M 1/85 604/319 |
| 2015/0342682 A1 | 12/2015 | Bowe | |
| 2016/0166265 A1 | 6/2016 | Nita | |
| 2017/0296712 A1* | 10/2017 | Anton | A61M 5/329 |
| 2017/0354777 A1* | 12/2017 | Ofek | A61M 1/80 |

FOREIGN PATENT DOCUMENTS

| | | |
|---|---|---|
| CN | 1768874 A | 5/2006 |
| CN | 101088472 A | 12/2007 |
| CN | 201079423 Y | 7/2008 |
| CN | 101259296 A | 9/2008 |
| CN | 101868280 A | 10/2010 |
| CN | 102209516 A | 10/2011 |
| CN | 103932756 A | 7/2014 |
| JP | 9-53568 A | 2/1997 |
| JP | 2000-139934 A | 5/2000 |
| WO | 2014/151209 A1 | 9/2014 |
| WO | 2017/147493 A1 | 8/2017 |

OTHER PUBLICATIONS

Chinese Office Action and Search Report issued in Chinese Patent Application No. 201780059366.8 dated Jun. 15, 2021, with English translation of Search Report.

Notification of Reasons for Refusal issued in corresponding Japanese Patent Application No. 2019-504107 dated May 25, 2021 (English translation only).

Office Action and Search Report issued in Chinese Patent Application No. 201780059366.8 dated Apr. 22, 2022, English translation of Search Report.

* cited by examiner

CLOT RETRIEVAL SYSTEM FOR REMOVING OCCLUSIVE CLOT FROM A BLOOD VESSEL

CROSS-REFERENCE TO RELATED APPLICATIONS

This application is a United States national stage entry of an International Application No. PCT/EP2017/068759 filed Jul. 25, 2017 which claims priority to European Patent Application Serial No. 16181338.1 filed Jul. 26, 2016 and U.S. Provisional Application 62/474,383 filed Mar. 21, 2017. The contents of these applications are incorporated herein by reference in their entirety as if set forth verbatim.

FIELD OF THE INVENTION

This invention relates to devices intended for removing acute blockages from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

BACKGROUND

Despite a wealth of information in the literature on the clotting cascade and on the biochemistry and etiology of thrombus in humans, remarkably little information is available on the physical and mechanical properties of this material. These properties are very pertinent to the interaction between thrombus and clot retrieval catheters and devices and the surrounding vasculature during mechanical thrombectomy of vessels occluded by thrombus material. Through extensive experimentation and research into thrombus material the inventors have discovered aspects of the properties and behaviour of certain clot/thrombus types that help to explain why these clot types can be particularly challenging to retrieve. Some of these findings are described in our WO2012/120490A, the entire contents of which are herein incorporated by reference.

Clot is essentially a living polymer, comprising a matrix of intertwined and cross linked fibrin strands within which are situated red and white blood cells, platelets and numerous other proteins and components. The inventors have discovered that the mechanical properties of a clot are strongly influenced by the relative percentages of fibrin and red blood cells, and that clots with a high (and highly organised) fibrin content and low red blood cell content tend to be much firmer and more cohesive than clots of a higher red cell content. Such clots have also been found to have a higher coefficient of friction, or in other words to be "stickier". These firm and sticky clots can be very challenging to remove from a vessel.

Clots with a low fibrin content and high red cell content have been found to be less cohesive and more friable and to have a lower coefficient of friction than the more organised fibrin rich clots previously described. These properties mean that such clots may be easier to dislodge from the site of occlusion, but may tend to fragment during the retrieval process, with the consequent risk of loss of clot fragments into distal or new vascular territories.

Furthermore, the inventors have discovered that the fibrin matrix of the clot can result in the clot material exhibiting viscoelastic behaviour in certain circumstances. A series of experiments were carried out in which a range of clots of varying fibrin content were tested. The clot samples were held in a receptacle and an indentor was placed on the surface of the clot and subject to a fixed indenting force. The depth of penetration of the indentor into the clot was measured as a function of time for each clot type. Clots with a high fibrin content and low red blood cell content were found to exhibit the greatest viscoelastic effect, with the indentor effectively "creeping" into the clot over a period of several minutes, whereas with low fibrin content clots the indentor tended to almost fully penetrate the clots in a matter of seconds. greater levels of organisation (and clot maturity) of the fibrin structure resulted in firmer clots which were penetrated to a much lesser extent by the indentor.

This behaviour combined with the higher frictional properties of fibrin rich clots tend to make these clot types particularly challenging to retrieve by mechanical thrombectomy. Conventional stent-retrievers may find it difficult to penetrate and grip these firm clots, and the high level of friction they maintain with the vessel wall can result in a tendency for the clot to roll and compress.

Attempts to aspirate such clots into a catheter can also be very challenging as the clot must be deformed in order to fit into the catheter lumen, and the energy required to deform such clots is not easily attained by aspiration. The high frictional coefficient of these clot types adds further to the challenge of aspirating them into the distal mouth of a catheter. Even maintaining a suction grip on such clots so that they can be retracted to the safety of a more proximal guide or sheath is very difficult, as these firm clots do not tend to deform and reshape easily and thus do not readily conform to the shape of the catheter tip in order to effect a seal and consequent suction grip.

STATEMENTS OF THE INVENTION

This invention solves the challenge of aspirating fibrin rich clot material into a catheter by addressing the key challenges of 1) the friction between the clot and the catheter and 2) the energy/work required to deform these firm clots as they are aspirated into the catheter tip.

Conventional clot aspiration involves inserting a catheter (sometimes referred to as an intermediate catheter or aspiration catheter or distal access catheter) into the patient's vasculature and advancing the catheter up to the occlusive clot. A syringe or vacuum pump is then attached to the proximal end of the catheter and a vacuum applied to attempt to suck the clot into the catheter tip and out through the catheter. The level of the vacuum applied can be controlled to a very limited extent by the force applied to the syringe or by the pump setting, and typically a fairly constant pressure drop of 500 mmHg to 760 mmHg (or "full" vacuum) is applied. The difference in pressure between the blood vessel in which the clot is situated and the interior of the catheter creates a pressure gradient (which may exceed 760 mmHg as the patient's blood pressure is higher than atmospheric pressure) which urges the clot into the catheter mouth.

The diameter of the clot however is greater than the diameter of the catheter therefore for a clot to be aspirated into a catheter the clot must deform and elongate to fit into the catheter tip. The energy to deform the clot to fit into the catheter is effectively an extrusion energy as the catheter tip acts as a form of extrusion die for the clot. This extrusion energy is related to the fibrin content of the clot with higher fibrin clots requiring increased extrusion energy to aspirate the clot into the catheter. Current techniques to aspirate the clot involve applying a steady state vacuum to the tip of the catheter; however in many cases this does not provide sufficient energy to aspirate the clot fully into the catheter. Subsequent retrieval of the catheter either does not dislodge the clot or dislodges the partially retrieved clot and creates the risk of losing the partially exposed clot into a side branch or new vessel creating an ENT (Embolization in New Territory).

This invention improves the ability of a catheter to aspirate a clot fully, including clots which have higher fibrin content. As stated above, vacuum is applied to the catheter tip to create a pressure differential between the catheter and the blood vessel with the aim of aspirating or sucking the clot into the catheter and out of the vasculature. When the apparatus detailed in this invention is operating, the steady state vacuum normally applied at the tip of the catheter is modified to a pulsatile or wave configuration so that in one design configuration, the pressure differential between the catheter tip and the blood vessel plotted against time resembles a sine wave. The application of the aspiration force to the clot in a wave or pulsatile configuration applies an 'impact load' to the clot which can deform the clot and overcome the resistance or extrusion energy required to get the clot into the catheter more quickly and effectively than applying a continuous or steady aspiration force.

In addition, when clot occludes the distal tip of an aspiration catheter, part of the clot is inside the tip of the catheter. Testing has shown that compression and manipulation of thrombus increases the friction of the clot. Therefore compression of the clot at the tip of the catheter further increases the static friction between the clot and the inside surface of the catheter tip. The static friction between the clot and the catheter needs to be overcome to allow the clot to be aspirated fully into the catheter. The application of a pulsatile force to the clot can cause the clot to vibrate or move slightly proximally and distally, so that the interaction between the clot and the internal surface of the catheter changes from static friction to a dynamic friction interaction. Dynamic friction of clot has been shown in our testing to be lower than static friction therefore the total force to remove the clot is reduced when using the apparatus detailed in this invention.

The fibrin matrix of a thrombus is porous and red blood cells can migrate and flow within the matrix depending on pressure differentials and fibrin density. Applying a pulsatile energy or vacuum at the catheter tip can promote this movement of clot elements, allowing the red blood cells to be aspirated out of the fibrin matrix. The thrombus is then easier to aspirate as the red blood cell content of the clot decreases facilitating deformation of the fibrin matrix with reduced energy.

This invention is suitable for the aspiration of clots with varying fibrin content from 0% to 100%, and is particularly suited to the aspiration of clot or thrombus which has fibrin content greater than 30%. The invention relates to the removal of a blood clot from the human vascular system. In particular it more specifically relates to the removal of a blood clot from the neurovasculature including the anterior and posterior circulation. Techniques and means of removing blood clots, or clotted blood particles in the form of emboli are already well known and established in use. When the presence of a clot is identified in the body it may be treated by best medical treatment (BMT) in the form of medication or by surgical intervention. Surgical intervention can involve the use of mechanical means to dislodge and remove the clot. Blood clots may also be identified and referred to as emboli. Surgical intervention may be in the form of minimally invasive endovascular intervention where by the clot or embolism is accessed within the blood vessel by the distal end of a catheter that has been introduced within the arterial system at a remote location such as the Common Iliac artery. This is well known and relevant to the background of this invention.

Referring to an endovascular intervention described herein one of the means used to effect the removal of a clot through surgical endovascular intervention, is to use what is commonly referred to as 'aspiration' of the clot mass through a catheter. Aspiration is a technique whereby negative pressure or suction can be applied to the clot mass within the blood vessel through the distal end of a catheter, the catheter being connected at the proximal end to a vacuum source.

It is well known that there are clots which cannot be moved or removed even with the maximum intensity of vacuum or aspiration being applied to them. The present invention relates to but is not limited to this situation and to the removal of these types of arduous blood clots. This invention presents and describes a method of removing blood clots by applying a pulsatile energy comprising of a sequence of alternating forces through the distal tip of a catheter which is adjacent to or abutting the blood clot wherein this sequence of pulsatile forces applied to the clot and having the effect of deforming the clot in addition to aspirating the clot back through the catheter. The pulsatile force may also be described as being in the form of a sequence of pulses applied to the clot over a period of time, commonly referred do as frequency. Each pulse comprises of a sequential positive and negative volumetric displacement of fluid at the catheter distal tip. This cyclical positive and forward projecting pressure followed by negative pressure can be described mathematically in general but not limited to a sinusoidal function.

It is known that the aspiration function applies a negative force in the form of negative pressure of approximately 500-760 millimetres of mercury (mm Hg) at the tip of the catheter creating a flow from the distal to the proximal end of the catheter and recovering the content of this flow in a container which is part of the circuit and located close to the vacuum source. This pulsatile sequence of positive and negative pressures are applied through the catheter in conjunction with the aspirated negative pressure. The source of the pulsatile force is separate and independent of the source of the aspirated suction.

Waveforms which represent the sequence of pulsatile positive and negative pressures constitute inventive steps.

It is well known that there are clots which cannot be moved or removed by the level of aspiration being applied to them. The present invention relates to the removal of these types of clots. The invention describes in method of applying pulsatile force through a catheter at the distal tip to the clot which has the effect of aspirating the clot in one or more pieces and retrieving it into the catheter. The pulsatile force is in the form of a sequence of pulses applied to the clot over a period of time. Each pulse comprises of a sequential positive and negative volumetric displacement of fluid at the catheter distal tip or varying negative volumetric displacements.

This period cycle of varying negative pressure can be described mathematically in general but not limited to a sinusoidal function. The pulsatile sequence of pressures are applied in conjunction with the application of a steady state negative pressure/suction force. It has also been observed as a further inventive step that the blood clot can be recovered by applying the pulse without any aspiration.

With regard to the sinusoidal profile of the pressure emitted at the tip of the catheter then the pressure profile may vary about a pure sine wave in the following ways. A sine wave can be described for this purpose as having four components to it which are equal in frequency and amplitude but may be positive or negative. If the first part of the wave is an increasing pressure induced by the forward motion of a piston then the second part will be a negative pressure caused by a reverse motion of the piston. The piston is driven by a shaft or connecting rod that is rotated in a cycle along the length of the shaft and thus directing the piston in a forward and reverse motion. In terms of the since wave describing this motion the first part of the curve indicating the increasing pressure is referred to as the rise time. The next part of the curve which represents a reverse motion of the piston and results in negative pressure at the catheter tip, this is referred to as the fall time or the decay time. The curve has one positive peak and one negative peak in each cycle. In a sequence of cycles constituting a sequence of pulses, the time from peak to peak is the same in a sine wave. The peak of a sine wave can be said to have no duration as the intensity or amplitude of the wave is changing continuously even as it transitions from positive to negative.

The present invention describes wave profiles applied at the catheter tip which can be at variance to a pure sine wave in the following manner. One is that the rise time may not be equal to the decay time. The rise time may be longer or shorter duration that the fall time duration. Secondly the peak of the wave may have a duration or a dwell time. The purpose of the dwell time is to allow fluid or blood some time to fill into the space in the piston chamber or time to pass through the orifice at the end of the chamber.

The nature of the pulse applied to dislodge and retrieve the blood clot can be defined by the following variables or control aspects:
 Reciprocation
 Frequency
 Amplitude
 Rise time
 Dwell time
 Decay/Fall time While the application of the reciprocal motion of both positive and negative displacement in sequence is not well known, there are a number of methods available that are well known for reciprocal motion as described.

One is a purely mechanical cyclical drive system whereby the moving piston within the chamber is connected to crank shaft or the outer radius of a disk which is rotated so as to drive the piston to and fro. This to and fro distance is known as the stroke length. It is well known to use this method in positive displacement pumps but not positive and negative displacement in sequence.

Another well known method of generating reciprocal motion is by electromechanical means using electromagnetic induction whereby a magnetic field is induced in a coil of wire or alternately in two coils of wire for more control over different forces in each direction to create the forces necessary to move the piston to and fro in the chamber The source of the power can be an alternating current and voltage or a direct current whereby the positive and negative cycles are achieved by switching mode control circuit.

As mentioned heretofore the cyclical motion which results in a symmetrical sinusoidal wave form of positive and negative pressure is the simplest. It may be desirable to alter the shape of the wave form so that the negative pressure is greater than the positive pressure or so that the rate of increase in pressure is greater of less than the rate of decline in pressure. It is recognised herein that there may be an advantage in having no or less positive pressure than negative pressure so that vibration of the clot mass is reduced. It is recognised and presented as an inventive step that the introduction of dwell time on the peak and the trough of the wave form allows time for the fluid displacement to take place on both the positive and negative parts of each cycle. This is more relevant and important as the frequency of the cycles increases.

According to the invention there is provided a system for removing occlusive clot from a blood vessel comprising a vacuum source and collection chamber, a catheter to communicate the negative pressure to the location of the clot, and an apparatus to modify a steady state vacuum provided by a vacuum source to a series of pulses or a waveform configuration. In one iteration this apparatus contains a mechanical drive system whereby a moving piston within a fluid chamber is connected to crank shaft or the outer radius of a disk which is rotated so as to drive the piston to and fro creating a positive and negative fluid displacement in sequence. This variable fluid displacement is combined with the steady state vacuum or negative displacement provided by the vacuum pump to produce a waveform pressure differential between the catheter and the blood pressure at the tip of the catheter adjacent to the clot in the vasculature.

In one iteration the reciprocal motion to create the positive and negative fluid displacement is generated by electromechanical means using electromagnetic induction whereby a magnetic field is induced in a coil of wire or alternately in two coils of wire for more control over different forces in each direction to create the forces necessary to move a piston to and fro in the fluid chamber.

In another iteration the fluid displacement is generated by moving the piston using other electromechanical means such as the piezoelectric effect.

In another iteration the fluid displacement is generated using other mechanical means such as a pneumatic drive.

In one configuration of the invention, the apparatus to create the pulsatile or waveform pressure differential is separate to the vacuum pump and chamber and is connected through tubing and connectors. In another iteration the apparatus of the invention and the vacuum pump are integrated in a single unit.

In one embodiment of the invention the piston to generate the pressure differential at the catheter tip is located within the catheter body which acts as the fluid chamber. The piston is moved proximally and distally in the catheter through a linear connection to a drive system located at the proximal end of the catheter. Alternatively the piston is moved in the catheter through electronic means positioned within the catheter.

In one configuration of the invention, the apparatus to create the fluid displacement to produce a waveform pressure differential contains a single piston in a fluid chamber which is moved forward and back using a mechanical or electromechanical drive. In a different configuration of the apparatus multiple fluid chambers with pistons are connected to facilitate complex waveforms. The displacement output of the apparatus can then be a summation of the displacements of each piston which can be programmed to operate independently.

In one iteration of the device the piston used to create the fluid displacement is similar to a syringe with a moving seal between the piston and the fluid chamber. In another iteration other known hydraulic cylinder configurations are used to produce different waveform configurations.

In another iteration of the invention the tip of the catheter is vibrated by electromechanical means to reduce the friction between the catheter and the clot and help overcome the extrusion or deformation energy required to aspirate the clot. The catheter tip vibration can be combined with a large aspiration lumen with a cross sectional area greater or equivalent to a 0.030" diameter lumen and in the preferred embodiment has a cross sectional area greater or equivalent to a 0.040" diameter lumen. The catheter with the vibrating tip may be used with a steady state aspiration vacuum or with the waveform pressure differential as described elsewhere in the patent. The frequency of the tip vibration may range from 5 Hz to ultrasonic frequencies of greater than 20,000 Hz.

Also according to the invention there is provided a method of removing occlusive clot from a blood vessel comprising the steps of:— providing a guide catheter or sheath and an intermediate catheter, the intermediate catheter having a distal mouth and being configured such that it is advancable within the lumen of the guide catheter;

inserting the guide catheter into a first vessel proximal of an occlusion;

connecting the proximal end of the intermediate catheter to an aspiration source which consists of a vacuum pump, a collection chamber and the apparatus of the invention;

advancing the intermediate catheter through the lumen of the guide catheter until the tip of the intermediate catheter extends distal of the guide catheter into a vessel adjacent to the occlusion;

applying steady state aspiration to the proximal end of the intermediate catheter;

the intermediate catheter being configured to direct said aspiration through the distal lumen of the intermediate catheter to aspirate the clot into the mouth of said intermediate catheter.

If the clot is not aspirated switch on the apparatus of the invention to provide a waveform pressure differential between the catheter and the blood pressure surrounding the clot. The waveform pressure differential overcomes the extrusion energy of the clot and reduces friction between the clot and the catheter so that the clot can be aspirated through the intermediate catheter into the collection chamber and out of the vasculature.

In one embodiment of the invention, this waveform resembles a sine wave with a fixed frequency and amplitude, and equal rise and decay times.

In another embodiment of the invention, the frequency or time between peaks of the waveform may vary and increase or decrease with time. A repeating frequency pattern may also be utilised such as multiple high frequency pulses followed by a number of low frequency pulses.

Similarly in another embodiment the amplitude of the waveform may vary with time and consist of increasing or decreasing amplitudes or a combination of different amplitude pulses.

In another embodiment the rise and decay times of the waveform may vary such that the decay time is shorter than the rise time or vice versa, or a combination of different rise and decay times may be beneficial in aspirating the clot, for example, a saw tooth waveform.

Another wave pattern utilised in an embodiment of the invention is a truncated or square wave pattern where a dwell time is incorporated into the wave cycle at the peak or trough of the wave or at both times. A dwell time may also be incorporated into a wave pattern at any point in the cycle, for example, producing a step wave pattern.

In another embodiment of the device the amplitude of the pressure differential is such that positive pressure may be applied to the clot for a fraction of the time of the wave cycle to increase the impact load applied to the clot.

In one embodiment of the invention the waveform is a combination of a number of the waveforms or features described elsewhere in this patent. In another embodiment, the invention may be programmable to apply specific pressure differential waveforms to the catheter tip which may be optimised for different clot types, for example, a pre-programmed optimized waveform may be applied for a fibrin rich clot which would be different to the waveform optimized for an erythrocyte rich clot.

Also provided are additional variants of this method, including:

A method as described above in which the waveform pressure differential is applied to the intermediate catheter as it approaches the occlusion for the first time.

An additional variant of this method is to apply the waveform pressure differential to the guide catheter or sheath if an intermediate catheter is not being used in the procedure. Alternatively the waveform pressure differential can be applied to both the intermediate catheter and the guide catheter at the same time.

The waveform or pulsatile pressure differential applied to the intermediate catheter described in this patent can also be used when the intermediate catheter is used in conjunction with a stentriever device. The waveform pressure differential reduces the friction between the clot and the catheter and helps to deform the clot. This gives additional benefits of reducing the shear forces acting on the clot as it is retrieved into the intermediate catheter by the stentriever device.

According to the invention there is provided a system for removing occlusive clot from a blood vessel comprising:—
  a catheter; and
  an apparatus for generating a pulsatile vacuum force to pulse the pressure gradient at a distal end of the catheter.

In one case the apparatus comprise a vacuum pump and a pulse generator.

In one embodiment the pulse generator is integral with the vacuum pump.

In another embodiment the pulse generator is separate from the vacuum pump.

The pulse generator in one case may be located between the vacuum pump and the proximal end of the catheter.

There may be a flexible tubing between the vacuum pump and the proximal end of the catheter.

In one embodiment the pulse generator is applied to the flexible tubing.

The pulse generator in one case comprises a reciprocating plunger.

The pulse generator in another case comprises a rotatable cam.

The cam may comprise an outer bearing to minimise drag on the tubing. The outer bearing may comprise a sliding outer layer.

In one case the flexible tubing is uniform cross section along the length thereof.

In one embodiment the flexible tubing is of variable cross section along the length thereof.

The system may comprise a controller for controlling the apparatus for generating a pulsatile vacuum source. The controller may be adapted or configured to vary the pressure over time in a waveform.

In one case the waveform has a fixed frequency and amplitude, and equal rise and decay times.

In another case the waveform has a varying frequency with time.

The waveform may have varying amplitude with time.

The waveform may have a different rise and decay time.

In one case the waveform rise and decay times change with time.

In some cases the waveform is a truncated or square waveform incorporating a dwell time at the peak and trough of each wave.

The waveform may incorporate one or more dwell times within each wave producing a stepped wave configuration.

The invention also provides a method for removing occlusive clot from a blood vessel comprising the steps of:— delivering a catheter to a location adjacent to an occlusive clot; and applying a pulsatile vacuum to the clot using the catheter.

The method in some cases comprises the step of varying the pressure over time in a waveform.

The waveform may have a fixed frequency and amplitude, and equal rise and decay times.

The waveform may have a varying frequency with time.

The waveform may have varying amplitude with time.

The waveform may have a different rise and decay time.

The waveform rise and decay times may change with time.

The waveform may be a truncated or square waveform incorporating a dwell time at the peak and trough of each wave.

The waveform may incorporate one or more dwell times within each wave producing a stepped wave configuration.

In one embodiment the system comprises a canister which is configured to receive aspirated blood or material.

In one case the system comprises a vacuum pump which is connected to the canister. The vacuum may be drawn through the canister.

In one embodiment the system comprises a first vacuum pulse generator. In one case the system comprises a second vacuum pulse generator. The vacuum pulse generators may be configured to operate separately, at the same time, or at different times to vary the vacuum pulse generated.

In one case the first pulse generator comprises a valve having a housing and an element which is rotatable and/or oscillatable in the housing.

In one case the second pulse generator is adapted to engage a flexible tube. The second vacuum pulse generator may comprise a rotatable cam.

In another case the first vacuum pulse generator comprises a pump. The system may further comprise non-return valves located on both sides of the pump.

In a further case the system comprises a canister configured to receive aspirated blood or material and the first pulse generator comprises an obturator which is movable through the canister.

BRIEF DESCRIPTION OF THE DRAWINGS

The invention will be more clearly understood from the following description of some embodiments thereof, given by way of example only, with reference to the accompanying drawings, in which.

DETAILED DESCRIPTION OF THE DRAWINGS

Specific embodiments of the present invention are now described in detail with reference to the Figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

Figure 1:
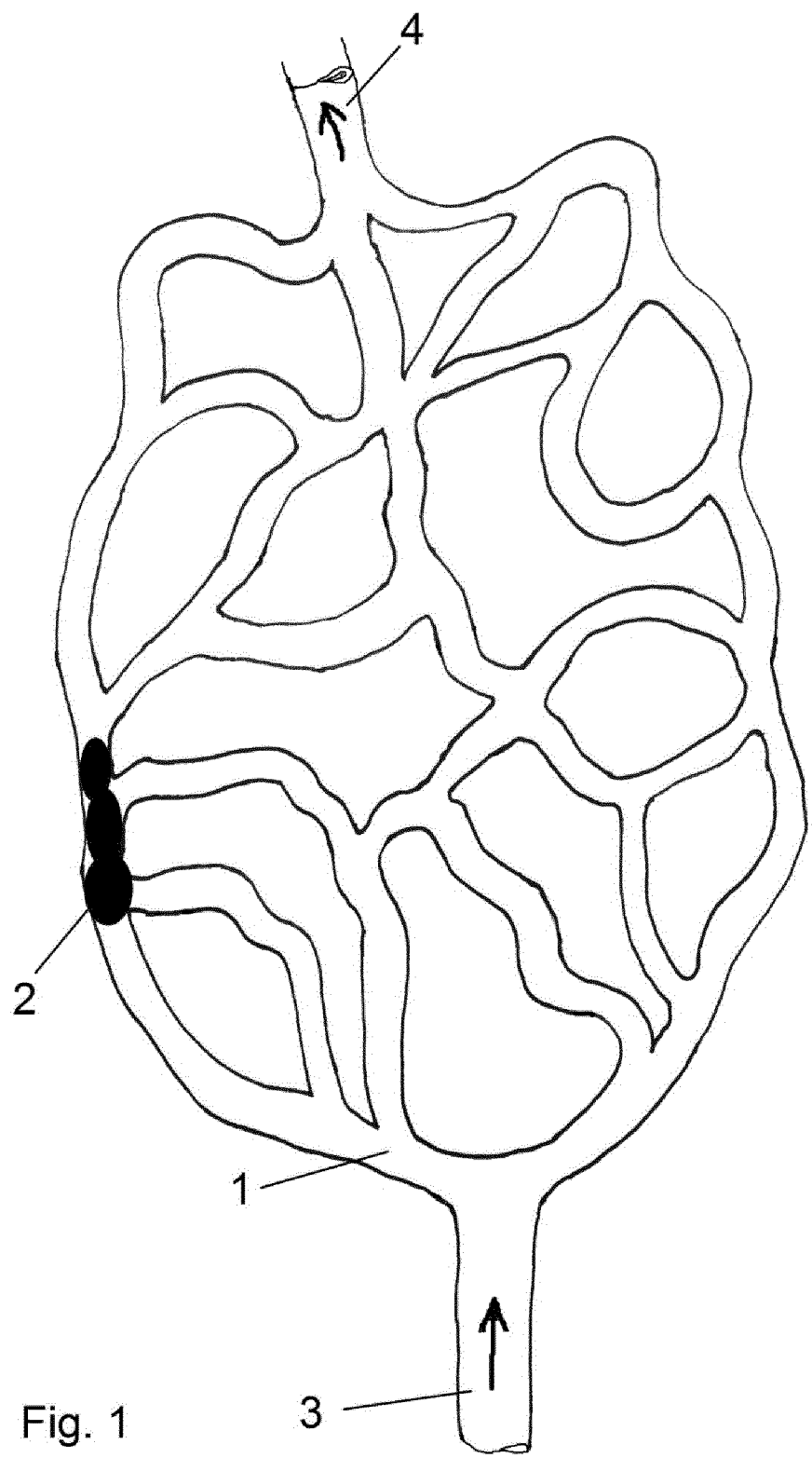
FIG. 1 is a view of a clot lodged in a representation of a similar cerebral vascular tubular network to the network in the brain for the purposes of describing the invention.

FIG. 1; Reference numeral 1 illustrates an example only of a lumen network similar in complexity to cerebral vasculature. Reference numeral 2 is an illustration representing a clot that is lodged in the cerebral vasculature network. Reference numeral 3 shows where the blood enters the network and reference numeral 4 shows where the blood exits the network.

Figure 2:
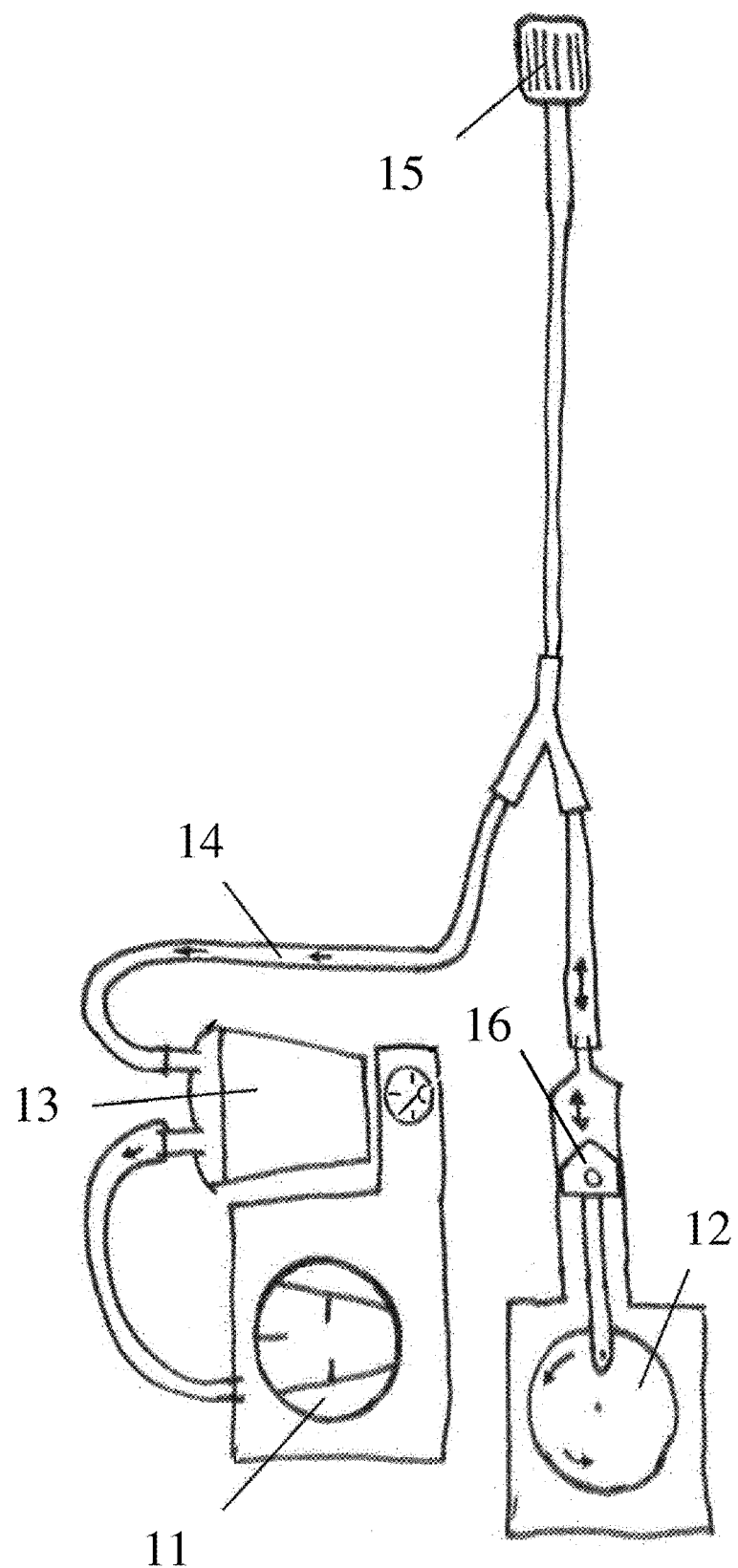
FIG. 2 illustrates by way of example only that the source of the aspiration or continuous negative suction and the source of the pulsatile pressure gradient are both combined to common effect through the catheter.

FIG. 2 illustrates a schematic representation of the steady state vacuum pump combined into a circuit with the pulse generation system. This circuit is then connected to the proximal end of a catheter. A vacuum pump 11 for creating aspiration suction represented by the approved standard drafting symbol. A cyclical reciprocation machine 12 is shown with a plunger 16 that moves to and fro in a piston chamber. A fluid collection container 13 within the aspiration circuit collects all the content aspirated from the body. Tubing 14 in the aspiration circuit is joined to the catheter proximal end at the same point where the reciprocation connects to the catheter proximal end. This is achieved using a Y junction connector. A connector 15 is provided for connection to the catheter proximal end. The catheter then passes through a haemostasis valve to enter the vascular system, usually at the common iliac artery (not shown here).

Figure 3:
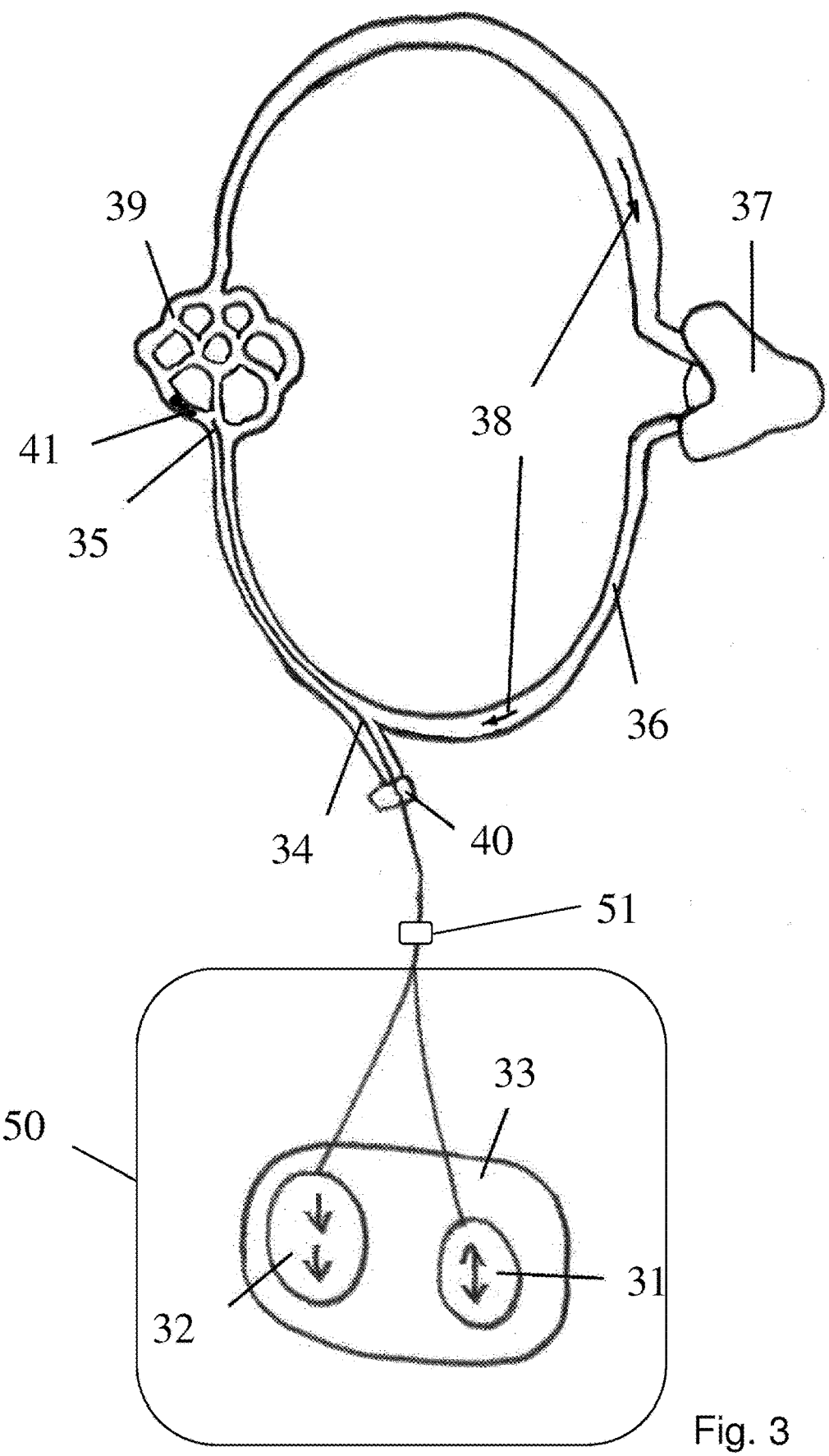
FIG. 3 shows the complete circuit interfacing with the circulation system in schematic form only.

FIG. 3 is a full schematic of the entire system including the vascular and cerebral circulation systems. The apparatus of the invention is shown in schematic form 50 and contains a steady state vacuum pump 32 and a pulsatile flow generator 31. The output of these pumps is combined and connected to the proximal end of a catheter 34 at the connector 51. The catheter is introduced into the vasculature at the haemostasis valve 40 and forwarded to the target location of the clot 41. When the catheter tip 35 approaches the clot 41, steady state vacuum from the pump 32 can be applied at the catheter tip. If the aspirate flow is blocked by the clot the pulsatile flow generator 31 can be engaged to produce a pressure differential waveform at the catheter tip to aspirate the clot 41.

Figure 4A:
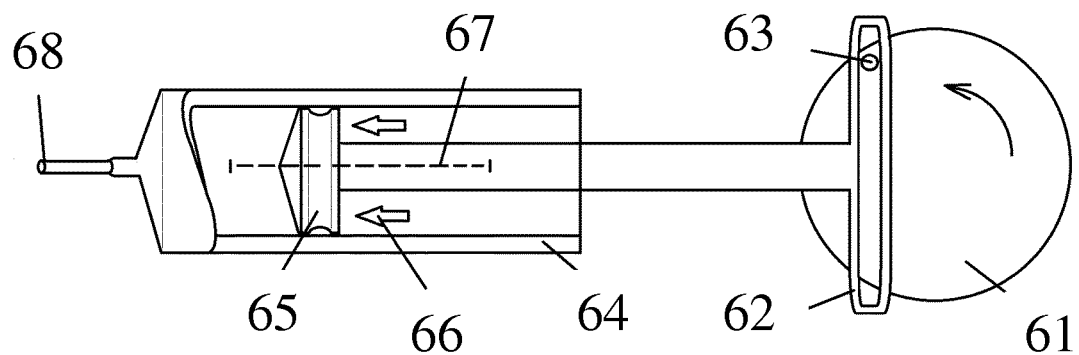
FIGS. 4A to 4C show by way of example only a means of generation cyclical motion which will generate the pressure differential waveform at the catheter distal tip.
Figure 4B:
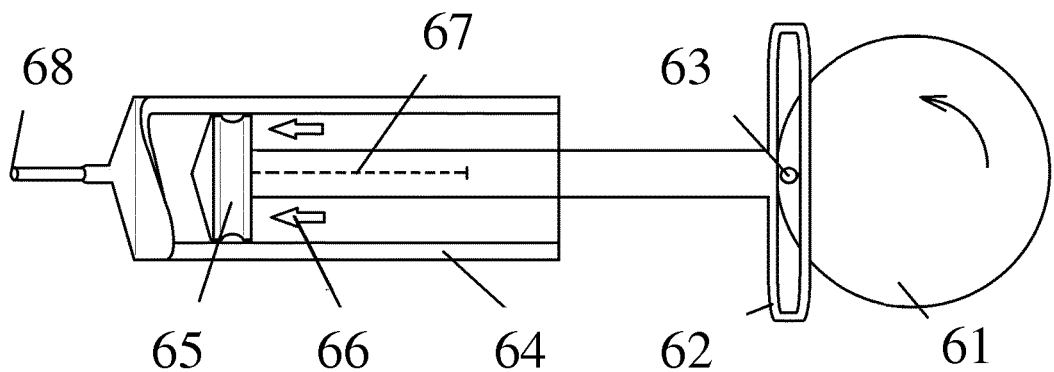
Figure 4C:
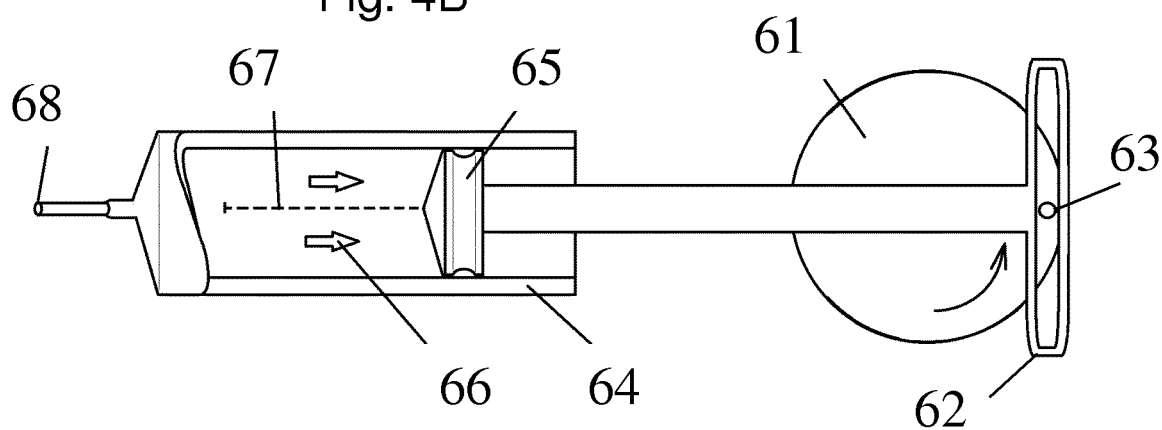
Figure 5A:
FIGS. 5A to 5E illustrate a number of possible wave form profiles representing positive and negative pressure pulses that are possible to generate with the reciprocation drive.
Figure 5B:
Figure 5C:
Figure 5D:
Figure 5E:

FIGS. 4 A to C are illustrations of a pulsatile flow generator that produces a pressure output which matches a sine wave configuration. A piston 65 is driven backwards and forwards by a rotating wheel 61 which contains a drive pin 63. This drive pin 63 engages in a slot of component 62, which is constrained so that it can only move in a linear direction. Therefore the rotational movement of wheel 61 is converted into linear motion of piston 65 which travels in the direction 66 as shown, as the wheel rotates. The fluid pressure output at 68 matches a sine wave.

FIG. 5 illustrates a number of possible wave form profiles representing positive and negative pressure pulses that are possible to generate with the reciprocation drive which have varying frequency.

Figure 6:
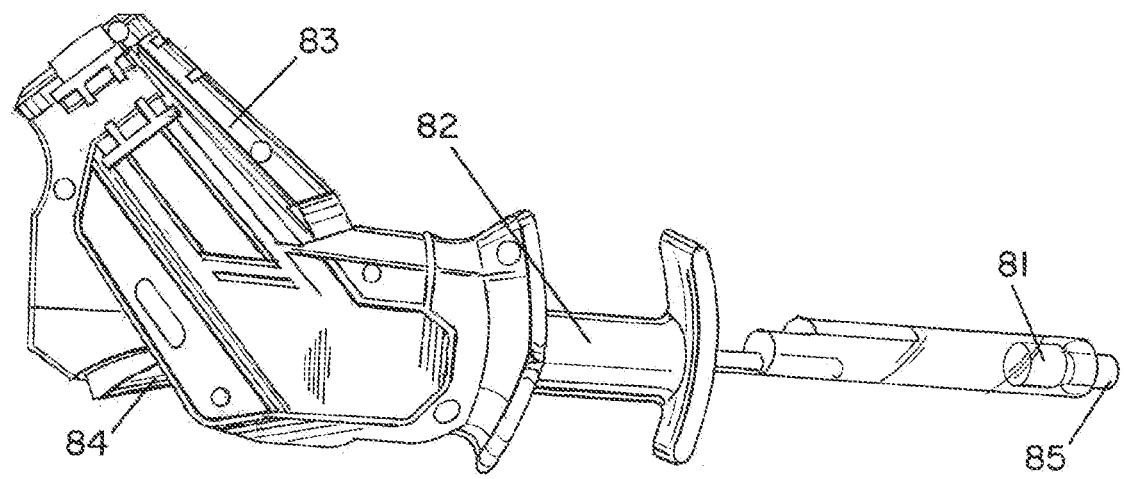
FIG. 6 is one example of a motorised reciprocal drive with variable speed.

FIG. 6 is one example of a motorised reciprocal drive 83 with variable speed. In this configuration the reciprocal drive shaft (not shown) is connected to the plunger of syringe 85. The drive is actuated using trigger 84 and moves the piston 81 backwards and forwards creating a pulsatile pressure output at the tip of syringe 85.

Figure 7:
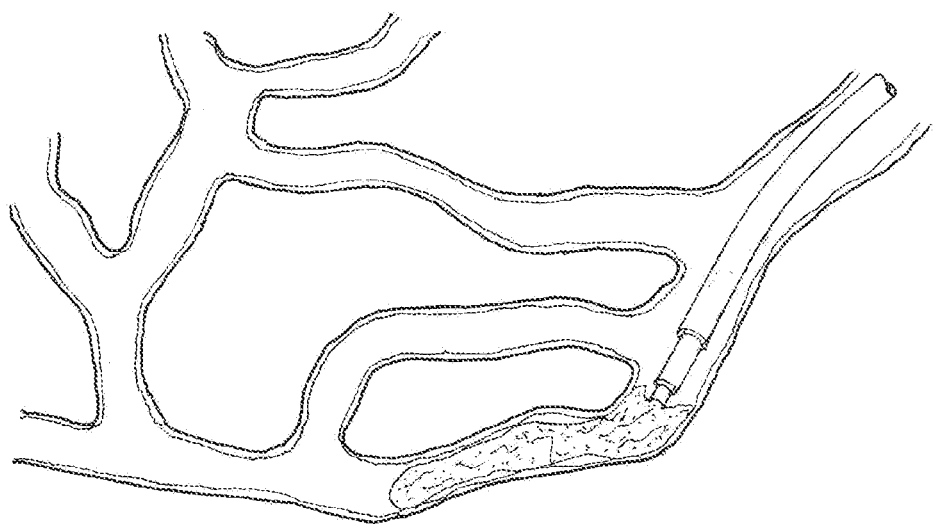
FIG. 7 shows the distal tip of a catheter touching or abutting a blood clot that is lodged in a circuit representing cerebral vascular complexity.
Figure 8:
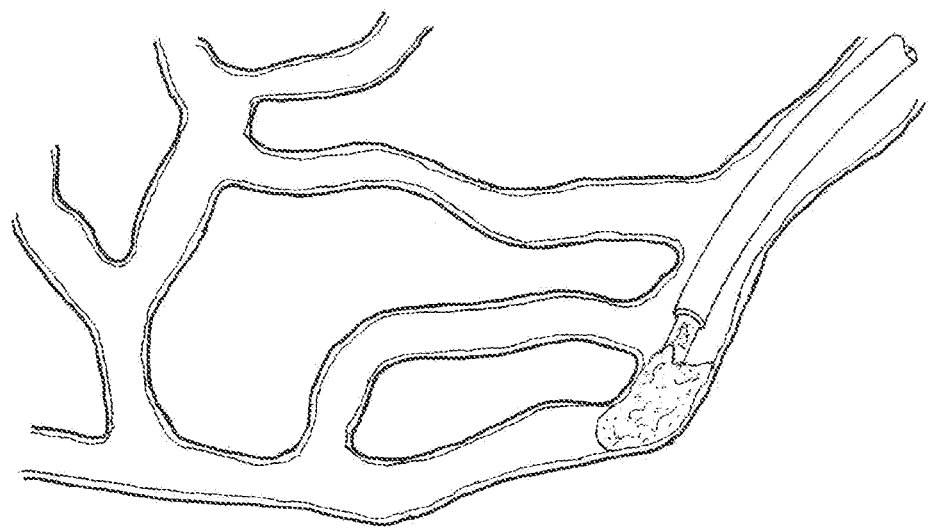
FIG. 8 shows the distal tip of a catheter firmly engaged in a blood clot that is lodged in a circuit representing cerebral vascular complexity—this is as a result of aspiration or suction at a rate of −500 mm Hg.
Figure 9:
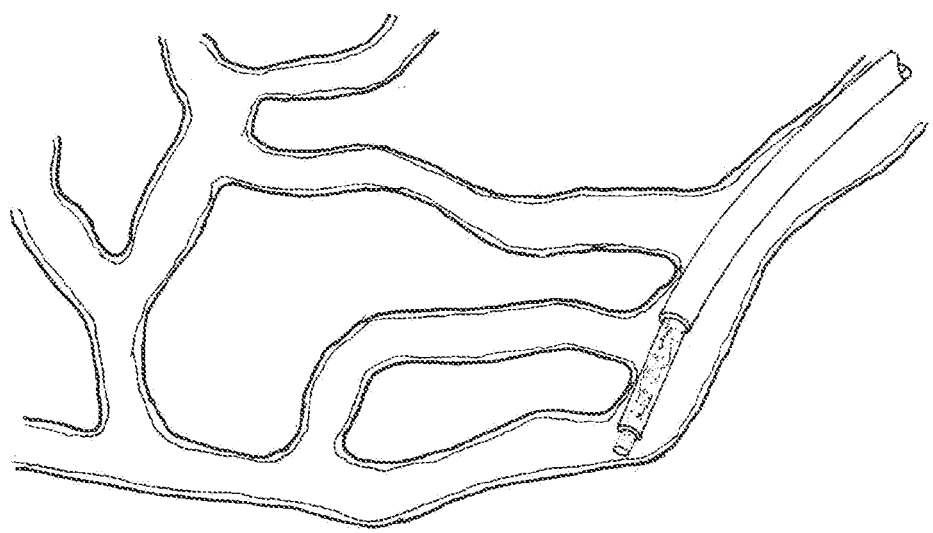
FIG. 9 shows that the clot in FIG. 8 has been aspirated into the catheter following a small number of reciprocation pulses (3 to 5)

FIG. 7 shows the distal tip of a catheter touching or abutting a blood clot that is lodged in a circuit representing cerebral vascular complexity. FIG. 8 shows the distal tip of the catheter firmly engaged in a blood clot that is still lodged in the circuit. In this example 500 mm Hg vacuum was applied to the catheter to aspirate the clot, however the application of this steady state aspiration energy was not sufficient to aspirate the clot. FIG. 9 shows that the clot in FIG. 8 has been fully aspirated into the catheter after a small number of reciprocation pulses (3 to 5) had been applied at the tip of the catheter.

Figure 10A:
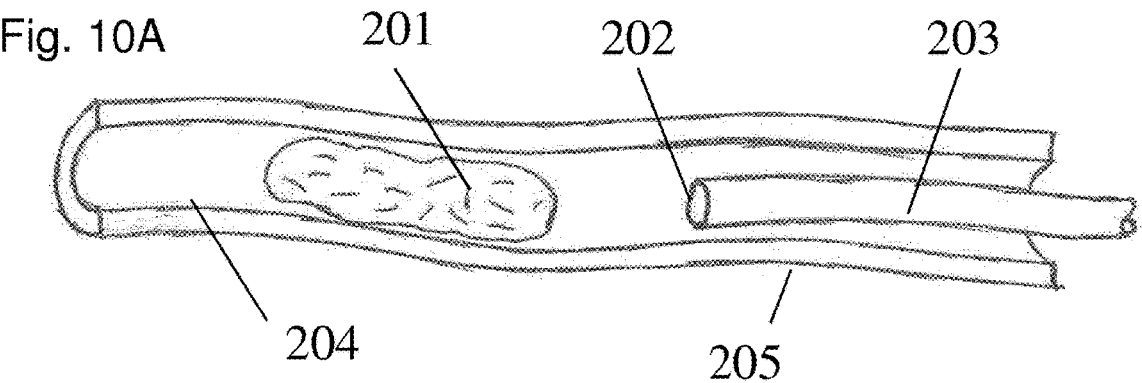
FIGS. 10A-D are schematic illustrations of a clot being aspirated into a catheter inside a blood vessel.
Figure 10B:
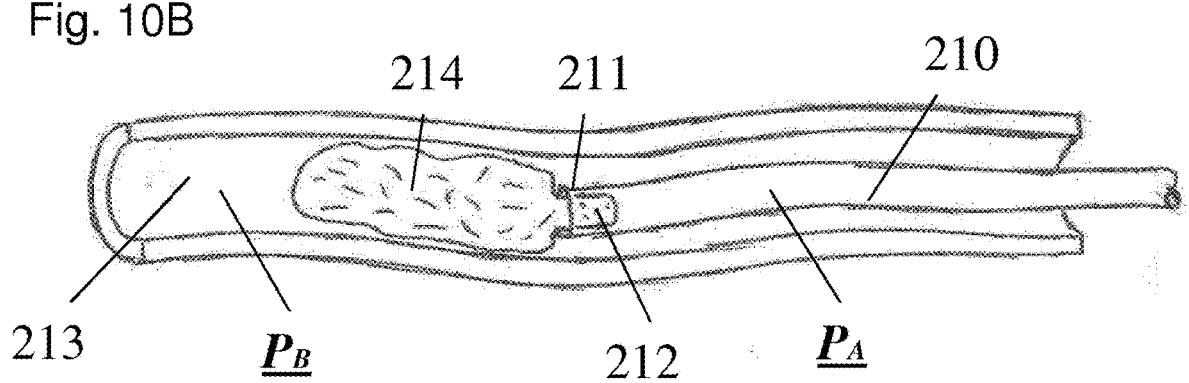
Figure 10C:
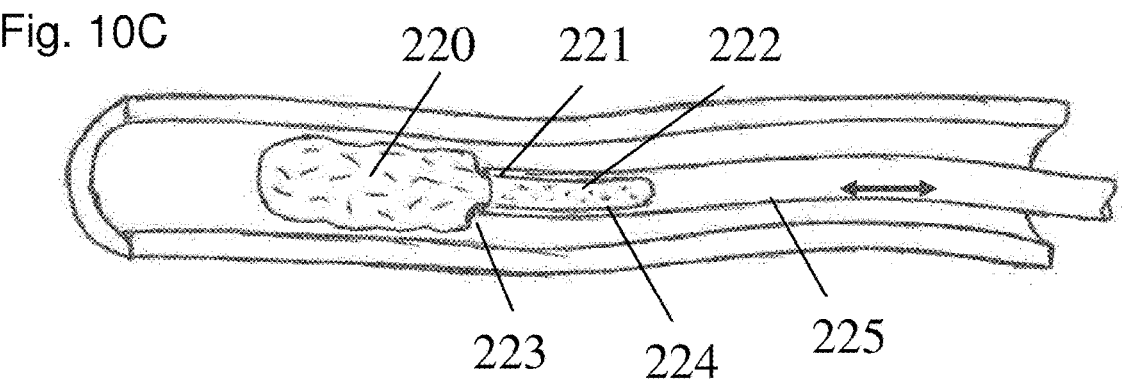
Figure 10D:
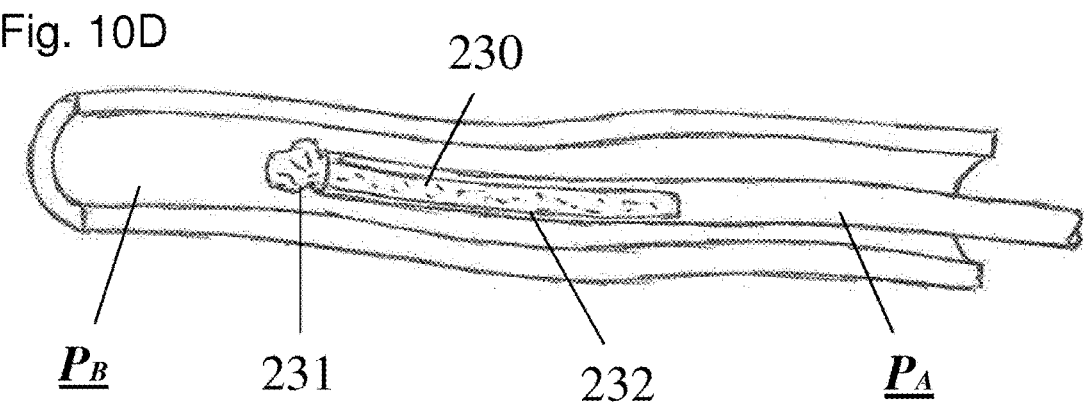

FIG. 10A shows a schematic illustration of an occlusive clot 201 lodged in a blood vessel 205. Catheter 203 has been introduced to the vasculature and the tip 202 is approaching the clot. FIG. 10B illustrates the catheter 210 in contact with the clot 214. A portion of the clot 212 has been aspirated into the catheter tip 211 blocking the tip and sealing the end of the catheter 210. As the catheter is blocked the pressure in the catheter $P_A$ is different to the pressure in the blood vessel $P_B$. The pressure differential acting across the clot is a function of $(P_B - P_A)$ and this urges the clot to deform and flow or extrude into the catheter. Applying a pulsatile pressure differential increases the energy applied to the clot and helps the clot to deform and flow. FIG. 10C illustrates that when a pulsatile pressure differential is applied to the clot 220 it can deform at the interface 223 where the clot enters the mouth of the catheter 221 to facilitate full aspiration. The friction between the clot 224 and the inner surface of the catheter 222 is also reduced by the application of the pulsatile pressure differential facilitating full aspiration of the clot. FIG. 10D shows the clot 232 approaching full aspiration into the catheter.

FIGS. 11 to 18 are a series of graphs of the pressure differential against time for a range of waveforms. The pressure differential $\Delta P$ is the pressure acting across the clot as shown in FIG. 10B and is related to the difference between the blood pressure in the vessel and the pressure in the catheter tip when the tip is occluded by the clot.

Figure 11:
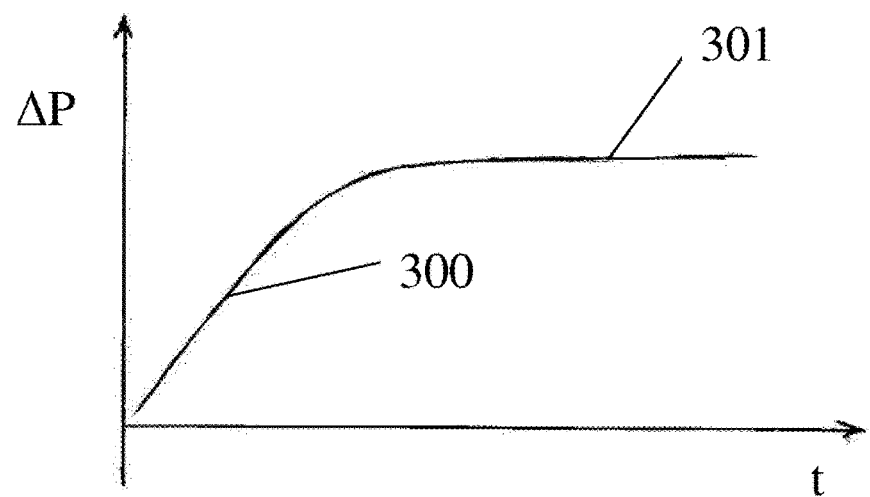
FIG. 11 is a graph of pressure differential against time for a steady state vacuum.

FIG. 11 shows a graph of pressure differential against time for a steady state vacuum. In this graph, the pressure differential increases 300 after the vacuum pump is switched on until it reaches a plateau 301 when steady state conditions are achieved.

Figure 12:
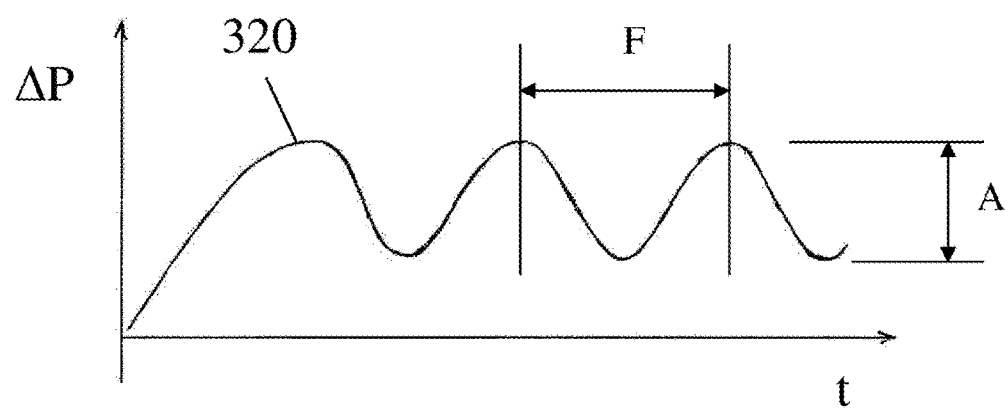
FIG. 12 is a graph of pressure differential against time for a pulsatile pressure differential waveform generated by the invention.

FIG. 12 shows a graph of pressure differential against time for a pulsatile pressure differential waveform generated by the invention. The graph 320 is similar to a sine wave with a fixed frequency (F) and amplitude (A).

Figure 13:
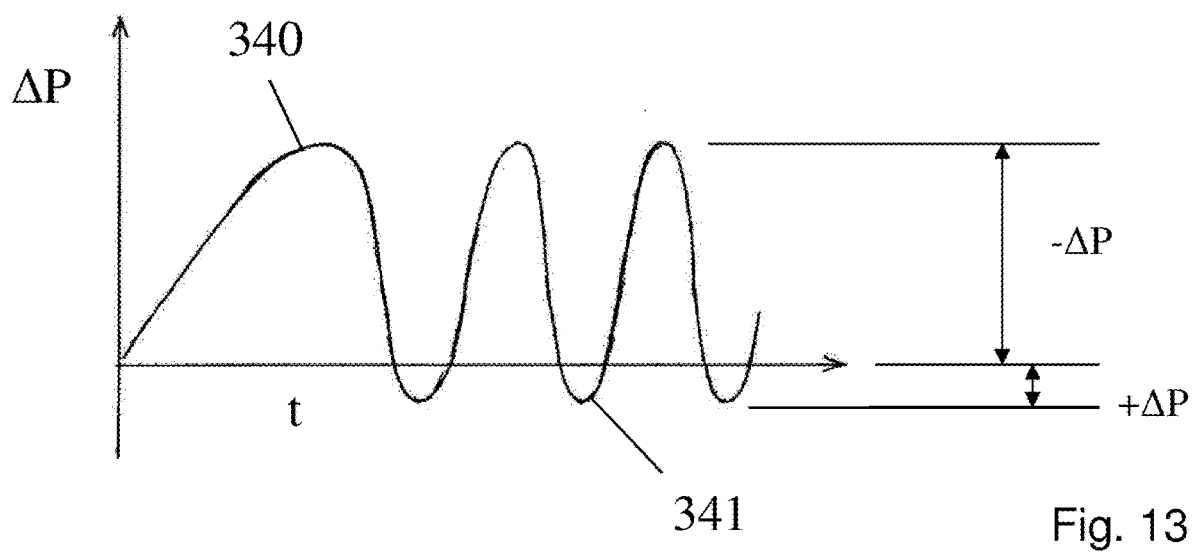
FIG. 13 is a pressure differential waveform with negative and positive pressure differentials.

FIG. 13 shows a pressure differential waveform 340 illustrating that during part of the wave cycle a positive pressure differential 341 is applied across the clot at the catheter tip.

Figure 14:
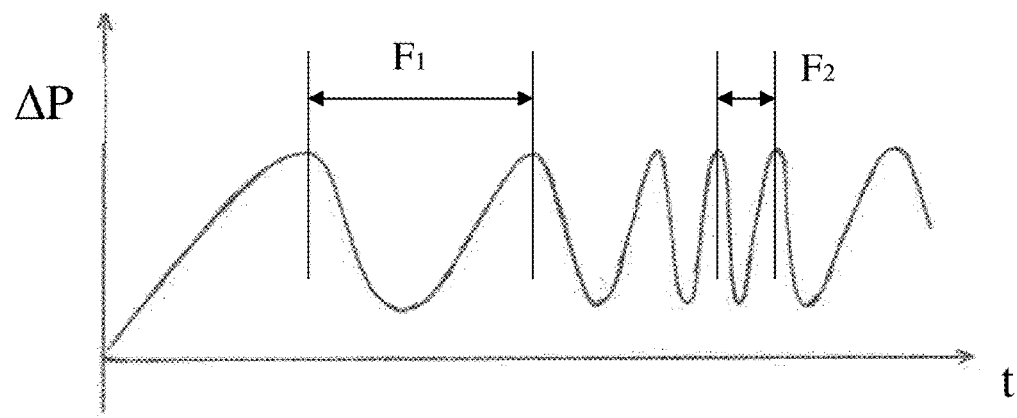
FIG. 14 is a pressure differential waveform with varying frequency.

FIG. 14 shows a pressure differential waveform with varying frequency where frequency $F_1$ is different to $F_2$ and is changing with time.

Figure 15:
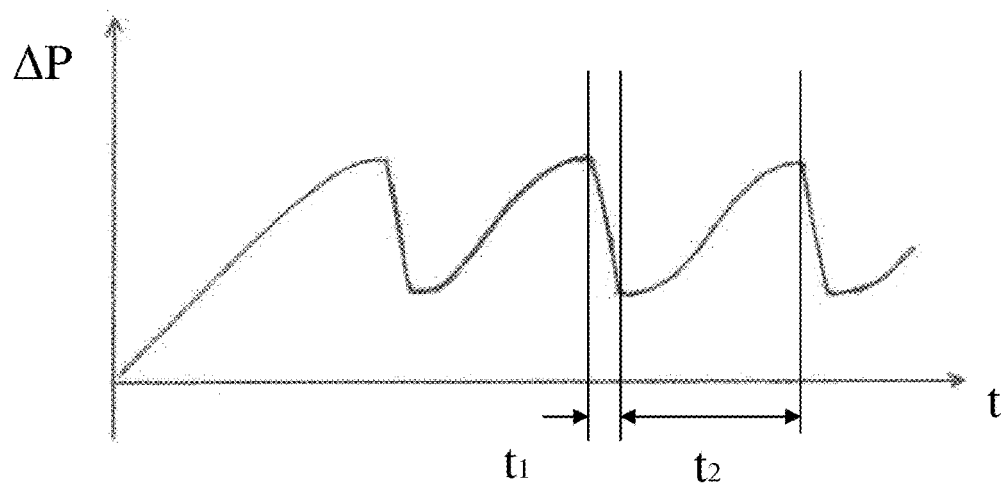
FIG. 15 is a pressure differential waveform with different decay and rise times.

FIG. 15 shows a pressure differential waveform with different decay and rise times. In the example shown the decay time $t_1$ is shorter than the rise time $t_2$ producing a saw tooth waveform.

Figure 16:
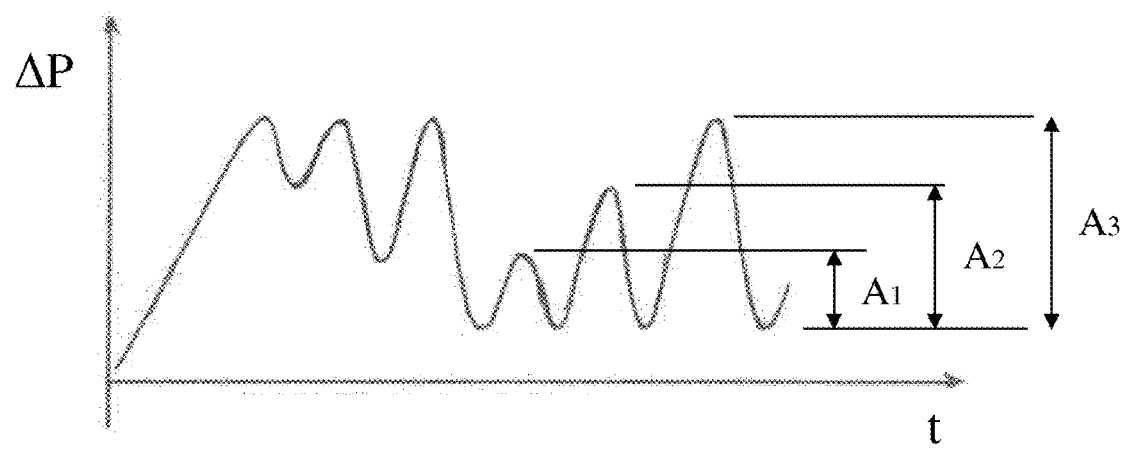
FIG. 16 is a pressure differential waveform with varying amplitude.

FIG. 16 shows a pressure differential waveform with varying amplitude. The absolute values of the amplitude can change with time as shown here where $A_1$, $A_2$, and $A_3$ are all different. The maximum and minimum values of the amplitude can also change with time.

Figure 17:
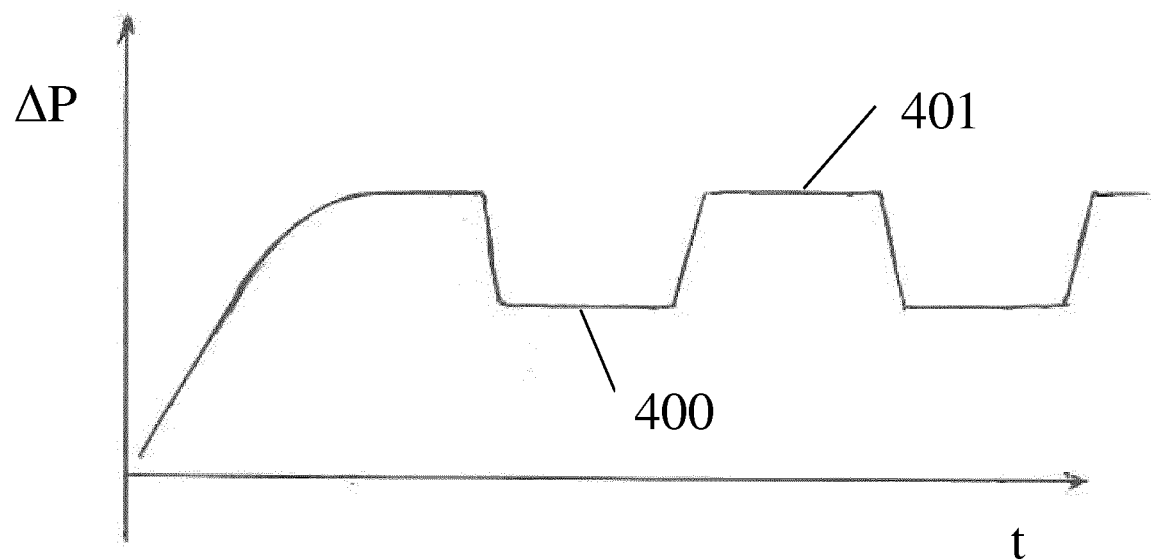
FIG. 17 is a pressure differential waveform with a truncated wave.

FIG. 17 illustrates a pressure differential waveform with a truncated wave. This waveform allows for dwell times 400 and 401 at the point of minimum and maximum pressure differential.

Figure 18:
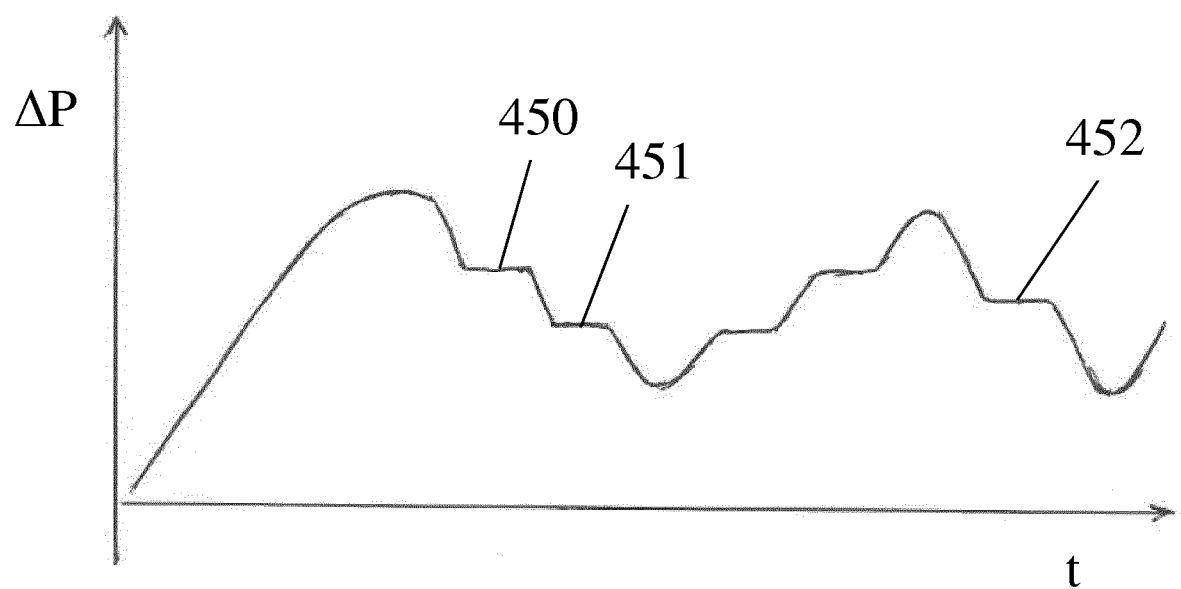
FIG. 18 shows a pressure differential waveform with a dwell time within the wave.

FIG. 18 shows a pressure differential waveform where a dwell time has been introduced within the wave. Multiple dwell times can be introduced in the cycle such as 450 and 451, or a single dwell time as shown 452.

Figure 19:
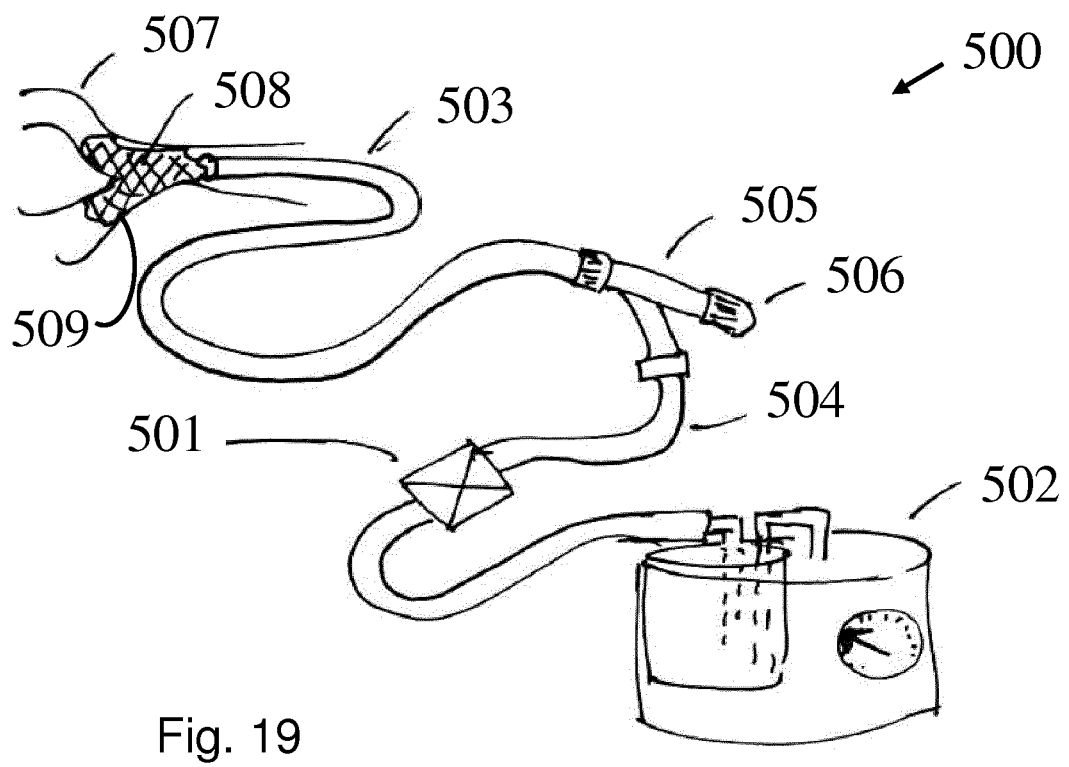
FIG. 19 is a diagram of a clot removal system of the invention.

FIG. 19 is an illustration of another configuration 500 of the invention. In this schematic a pulse generator (501) is a separate apparatus to a vacuum pump 502. This pulse generator 501 can produce a pressure differential waveform at the tip of the catheter 503 as described elsewhere in this patent but is non blood contacting. The pulse generator 501 creates the waveform by selective compression of connector tubing 504. This creates the benefit of not having to sterilise part of the apparatus prior to use, as the connector tubing 504 is disposable and single use only. The method of use is the same as that described before with the vacuum pump 502 and pulse generator 501 connected to the proximal end of the catheter 503 at a connector 505 with a proximal valve/seal 506. The catheter 503 is introduced through the vasculature to the target location in a vessel 507 of the clot 508. In this case a stentriever type clot capture device 509 is also shown.

Figures 20A, 20B, 20C:
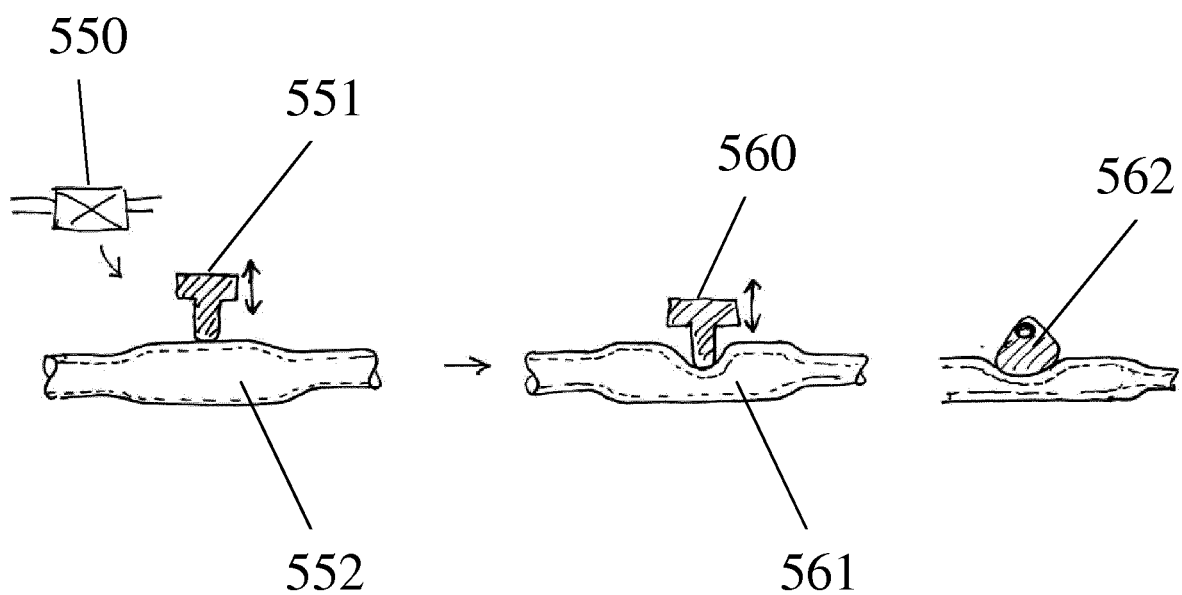
FIGS. 20A and 20B illustrate a piston type pulsatile vacuum generator.
FIG. 20C illustrates a cam type pulsatile vacuum generator.

FIG. 20A shows internal details of a pulse generator 550 such as that illustrated in FIG. 19. In this configuration a reciprocating plunger 551 can compress the tubing 552 creating a pressure wave. The tubing 552 is elastic and recovers its shape as soon as the plunger moves up. The stroke of the plunger 560 shown in FIG. 20B can vary and different plunger widths or multiple plungers can provide displacement variations. FIG. 20C shows a variation of this design where the plunger is replaced with a cam 562. Rotation of the cam provides a pulse generation capability.

Figure 21:
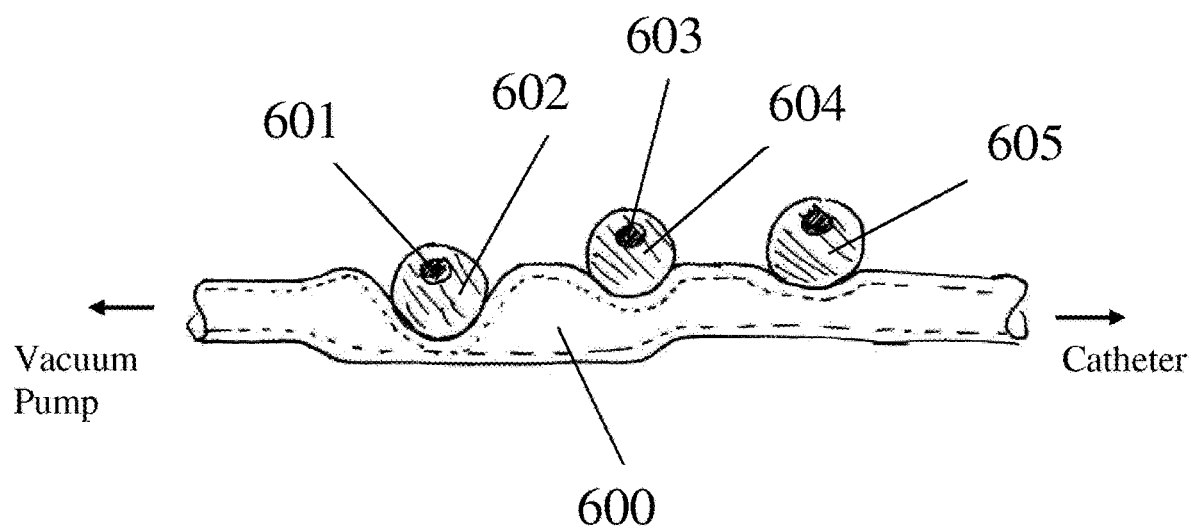
FIG. 21 is a view of another pulsatile vacuum generator.

FIG. 21 shows an advantageous design of the pulse generator which contains multiple cams in series. The cam 602 nearest the vacuum pump can rotate and seal the tubing 600 so that rotation of cams 604 and 605 can produce a positive pressure in the tubing. The tubing 600 is flexible and may be straight or have a stepped diameter as shown. The cams can be programmed so that some or all can work at any given time, each with a different frequency, or not be operated at all.

Figures 22A, 22B:
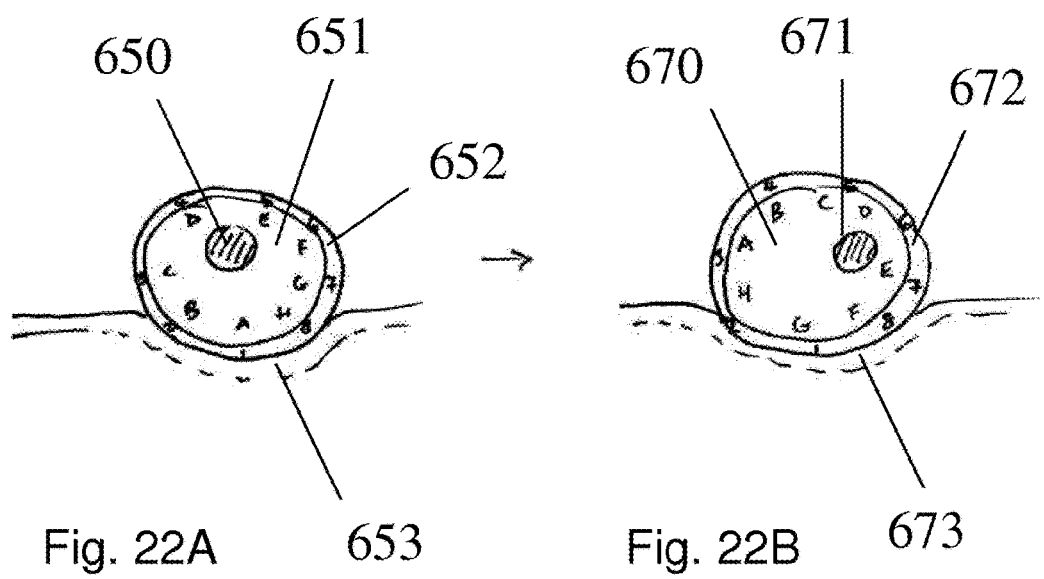
FIGS. 22A and 22B illustrate another cam type pulsatile vacuum generator.

To reduce friction between the cam and the flexible tubing, each cam could have a sliding outer layer as shown in FIGS. 22A and B. The cam 651 rotates on the eccentric axle 650 compressing the tubing 653. To reduce the friction the cam has a low friction sliding outer ring 652 which does not rotate relative to the tubing. FIG. 22B illustrates how the cam 670 position is rotated relative to FIG. 22A but the outer ring 672 has not rotated relative to the tubing wall 673.

Figure 23A:
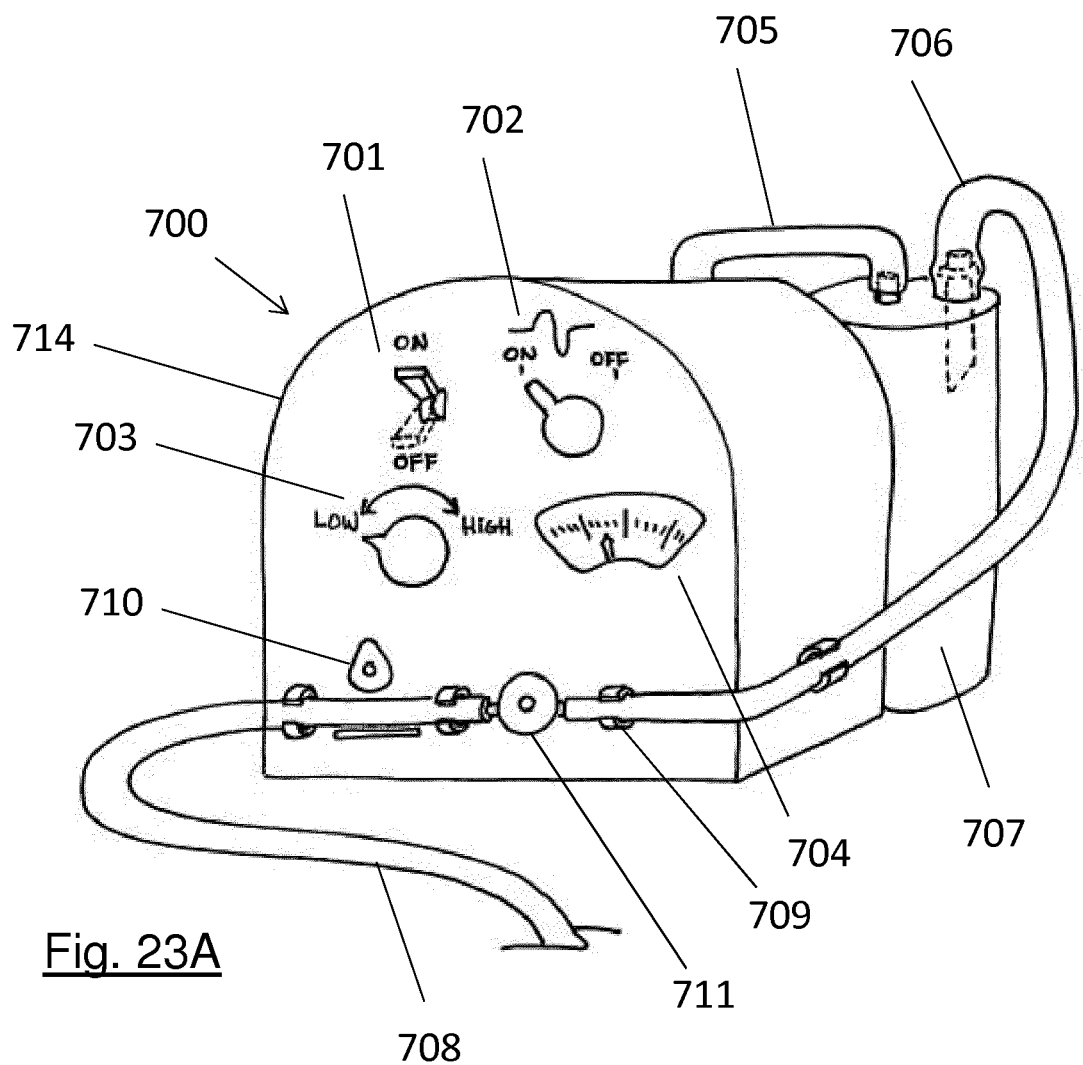
FIG. 23A illustrates a pulsatile aspiration system.
Figure 23B:
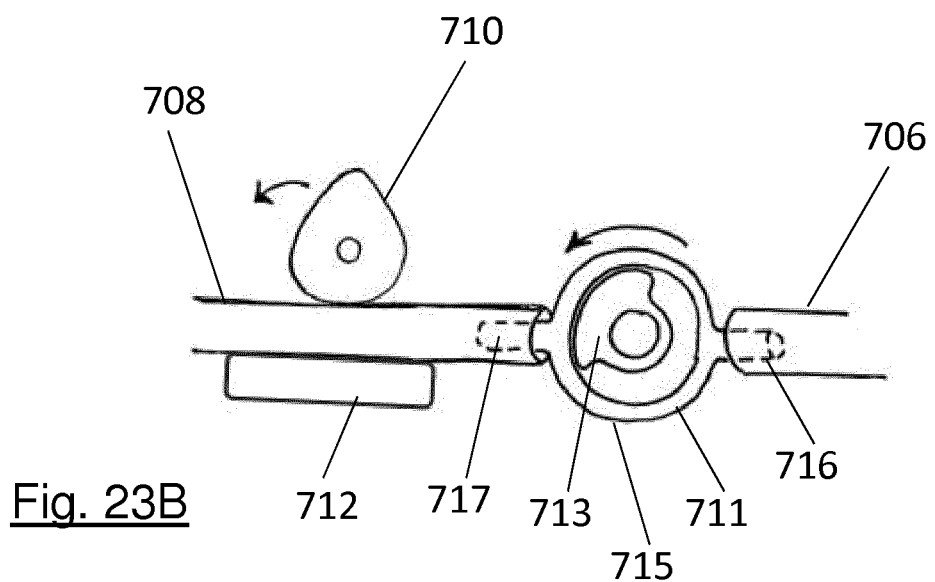
FIGS. 23B and 23C illustrate an element of the pulsatile aspiration system of FIG. 23A.

FIG. 23a illustrates an apparatus 700 of this invention, comprising a vacuum pump 714 and a pulse generating system. FIG. 23b shows a more detailed view of the pulse generating components of the system. The vacuum pump 714 may comprise a diaphragm or vane or piston pump, or a peristaltic pump, or other means of generating a negative pressure differential. This vacuum pump is connected by tube 705 to a reception canister 707, which is configured to receive aspirated blood or material. A safety valve may be provided within the canister to prevent fluid or material entering tube 705 and damaging the pump. Tube 706 connects the canister to rotating valve 711. Tube 708 connects rotating valve 711 to a catheter (not shown) that is inserted within the patient, and does so either directly or via a further connecting tube or connector or rotating haemostasis valve or similar. Tube 708 is held in place by clips 709, which are configured so that the assembly of tube 708, rotating valve 711 and tube 707 can be easily assembled to or detached from the system (so that they may be disposable elements of the system). When clipped into place tube 708 sits between a rotatable cam 710 and a support plate 712. In use the system is capable of supplying a steady state vacuum by means of the vacuum pump 714 once switch 701 is moved to the "ON" position. The vacuum pump evacuates the canister 707 via tube 705, and thus a suction or aspiration force is transmitted through tubes 706 and 708 (once rotating valve 711 and cam 710 are in the open position).

Figure 23C:
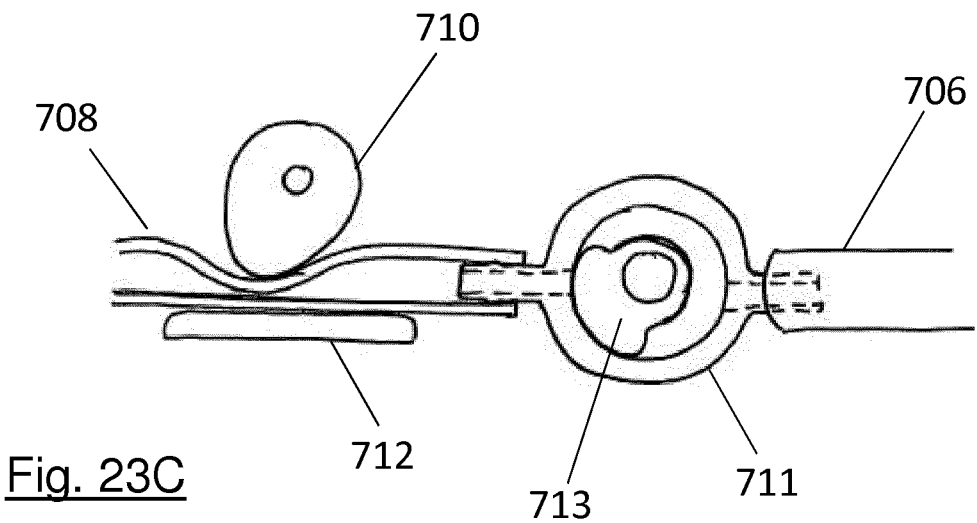
Figure 24A:
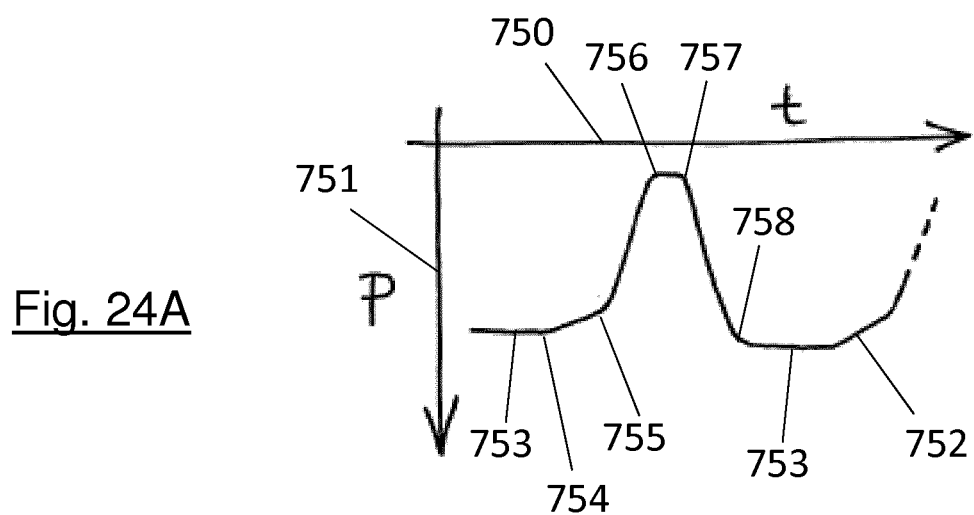
FIGS. 24A and 24B show pulsatile pressure waveforms.
Figure 24B:
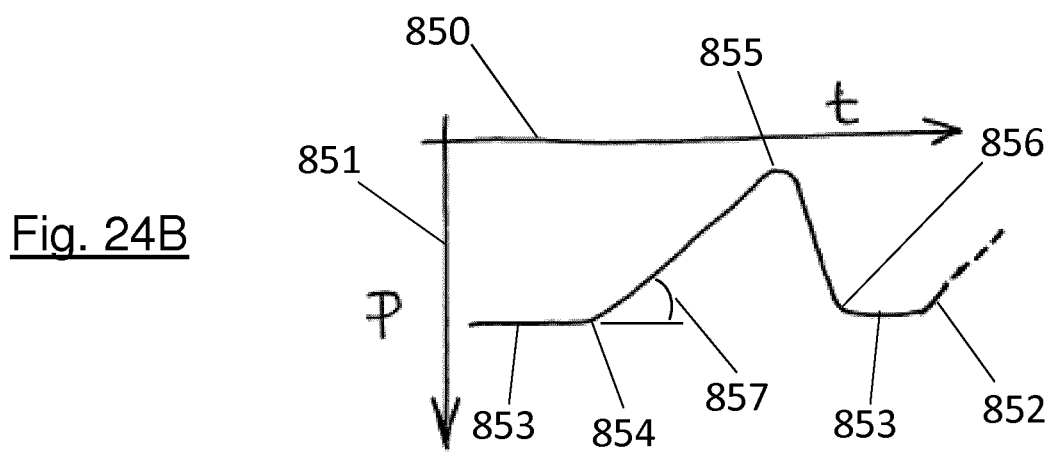

FIG. 23b and FIG. 23c illustrate the operation of the pulse generating system. Rotating valve 711 comprises a housing 715 with inlet and outlet tube connectors 717 and 716, and an internal rotating element 713. When rotating element 713 covers the mouth of either connector 717 or 716 the valve is closed and tube 708 is no longer exposed to the vacuum within canister 707. Thus by rotating or oscillating element 713 a vacuum pulse may be delivered through tube 708, and this may be beneficial for the retrieval of stubborn clot material as previously described. However the nature and condition of the material being aspirated may affect the waveform of the pulse generated in tube 708 and transmitted to the treatment catheter and thus to the patient. FIG. 24b illustrates a representative pulse generated by a vacuum pump with a simple on/off valve such as rotating valve 711. The vertical axis 851 denotes pressure and the horizontal axis 850 denotes time. Prior to initiating any pulse a relatively steady state vacuum level 853 is provided in tube 708. Closure of valve 711 disconnects the tube from the vacuum source. In a case (case 1) where the tube 708 is connected to a catheter which is aspirating liquid blood or very soft clot the closure of valve 711 will cause the vacuum in the catheter to decay quickly, and angle 857 will be steep, allowing the vacuum to decay quickly from level 854 to 855. Once valve 711 is opened the vacuum is restored and the vacuum level in the catheter quickly returns to original level 853. In a case (case 2) where the tube 708 is connected to a catheter which is aspirating a resistant material such as fibrin rich thrombus the closure of valve 711 will cause the vacuum in the catheter to decay more slowly than in the previous case, and angle 857 will be more shallow, so that the rate of decay of the vacuum is significantly reduced. A rate of change of vacuum level of greater than 100 mmHg/second is necessary in order to create an effective pulse in the catheter. A rate of change of greater than 200 mmHg/second is preferred, and a rate of change of greater than 400 mmHg/second is more preferred, while a rate of change of greater than 600 mmHg/second is most preferred.

The rotatable cam 710 and support plate 712 provide a means of increasing the rate of decay of the vacuum in tube 708 and any catheter to which it is connected, particularly in the scenario in which tube 708 is connected to a catheter which is aspirating a resistant material such as fibrin rich thrombus. This is achieved by creating a positive pulse of pressure to counteract the vacuum. This is achieved by rotation of the cam 710 to compress tube 708 between the cam and support plate 712, which in turn compresses the liquid or gas within tube 708 and thus rapidly reduces the vacuum level within the tube. FIG. 23c illustrates this compression in action. The cam may be timed to compress the tube 708 at the same time as valve 711 closes, or fractionally later than closure of valve 711. The cam 710 may be timed to release the compression of tube 708 before, simultaneously or after the opening of valve 711. The impact of this system on the pulsatile waveform generated is illustrated in FIG. 24a.

The vertical axis 751 denotes pressure and the horizontal axis 750 denotes time. Prior to initiating any pulse a relatively steady state vacuum level 753 is provided in tube 708. Closure of valve 711 disconnects the tube from the vacuum source. In a case (case 3) where the tube 708 is connected to a catheter which is aspirating a resistant material such as fibrin rich thrombus the closure of valve 711 will cause the vacuum in the catheter to start to decay slowly at a first rate of decay illustrated by the line between points 754 and 755. Rotation of cam 710 to compress tube 708 causes the rate of decay of the vacuum to be significantly increased, illustrated by the line between points 755 and 756. A dwell period may be provided between points 756 and 757, after which cam 710 is rotated to remove the compression from tube 708 and valve 711 is opened, allowing the vacuum level in tube 708 to drop quickly from point 757 to point 758. Again a dwell period may be provided at vacuum level 753 before additional pulses are provided.

Figure 25:
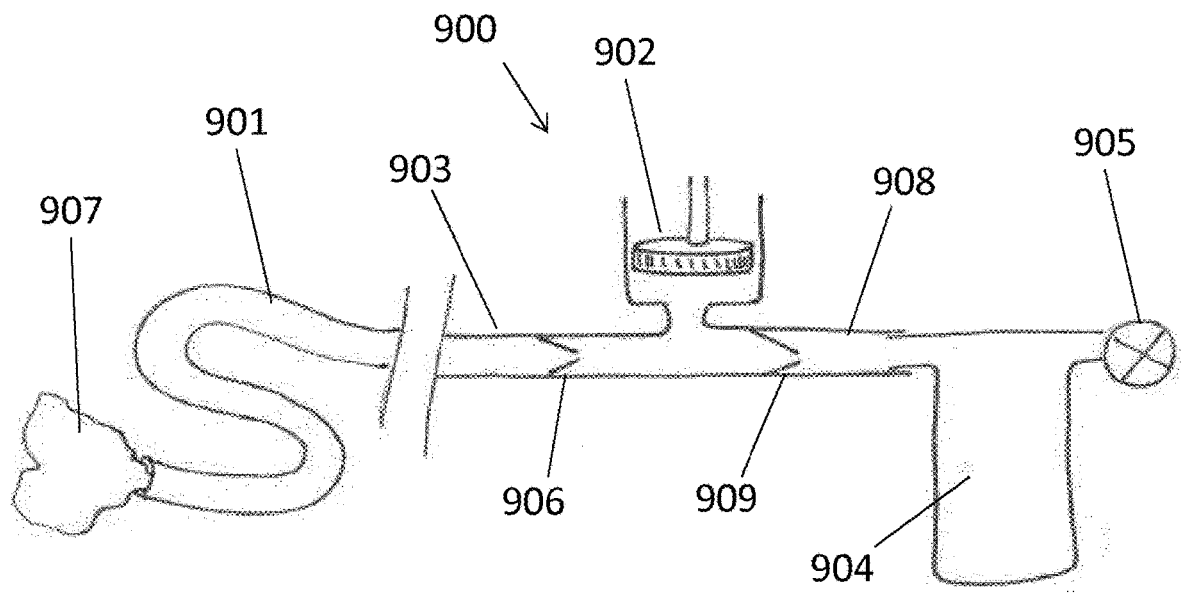
FIG. 25 is a schematic of another pulsatile aspiration system of this invention.

FIG. 25 is a schematic drawing of another pulsatile aspiration pump system 900 of this invention configured to provide pulses with a rapid rate of change of vacuum level. Catheter 901 is shown in the process of aspirating thrombus 907. This aspiration is caused by a pressure differential between the medium in which the thrombus is located outside the catheter and that of the internal lumen of the catheter. An aspiration force is provided to the catheter through tube 903, which is in turn connected to tube 908, which is itself connected to canister 904. Canister 904 is evacuated by pump 905. A second "pump" 902 is located between tubes 903 and 908 and consists in this embodiment of a piston pump, similar to a syringe. A pair of one way valves 906 and 909 are positioned either side of piston pump 902, so that when the piston moves downwards a small but limited positive pressure is applied to tube 903 and hence to catheter 901 before the valve 906 closes. This causes a rapid rate of change in the vacuum level within the catheter 901. Conversely when the piston moves upward the system will aspirate preferentially from the catheter rather than the canister, creating a rapid increase in the vacuum level within the catheter.

Figure 26:
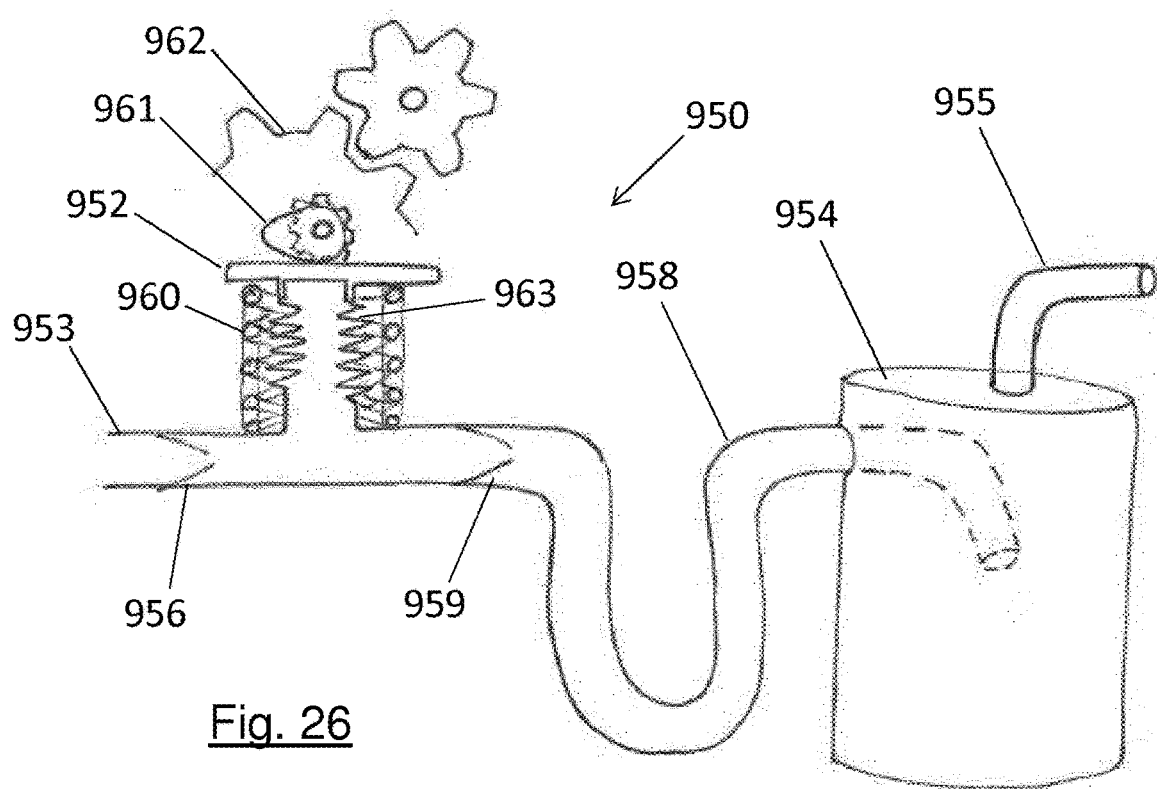
FIG. 26 is a schematic of a portion of another pulsatile aspiration system of this invention.

FIG. 26 is a schematic drawing of another pulsatile aspiration pump system 950 of this invention very similar to system 900. An aspiration force is provided through tube 953, which is in turn connected to tube 958, which is itself connected to canister 954. Canister 954 is evacuated by pump 955. A second "pump" 952 is located between tubes 953 and 958. Pump 952 consists in this embodiment of an oscillating diaphragm assembly 963, which is supported by compression spring 960 and actuated by the counteracting forces of this spring 960 and cam 961. Cam 961 may be operated by many means, including the gear assembly 962 illustrated herein. A pair of one way valves 956 and 959 are positioned either side of pump 952, so that when the diaphragm moves downwards a small but limited positive pressure is applied to tube 953 before the valve 956 closes. This causes a rapid rate of change in the vacuum level within the catheter 951. Conversely when the diaphragm moves upward the system will aspirate preferentially from the catheter rather than the canister, creating a rapid increase in the vacuum level within the catheter.

Figure 27A:
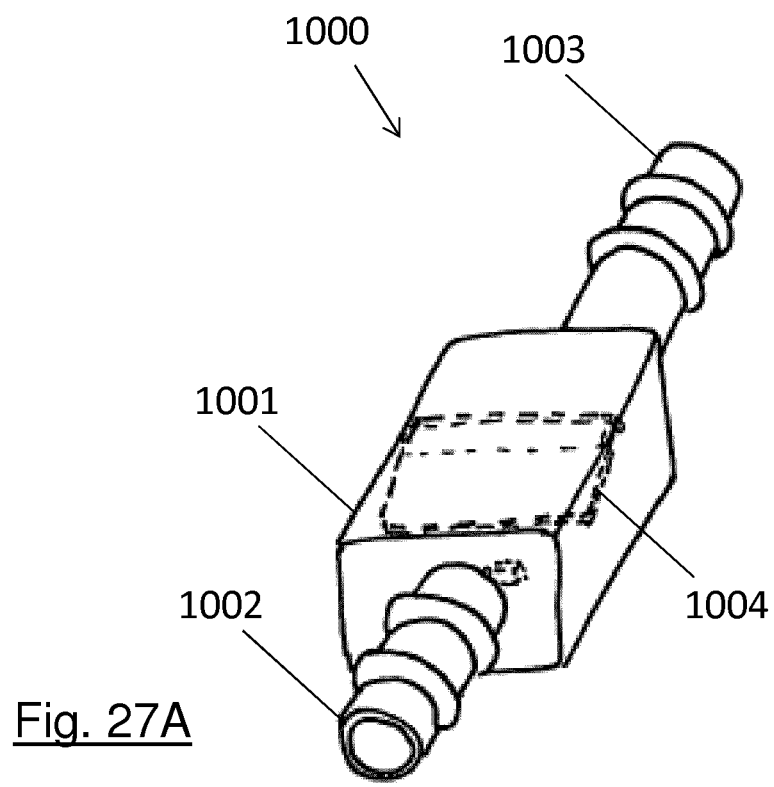
FIGS. 27A and 27B are views of a one way valve.
Figure 27B:
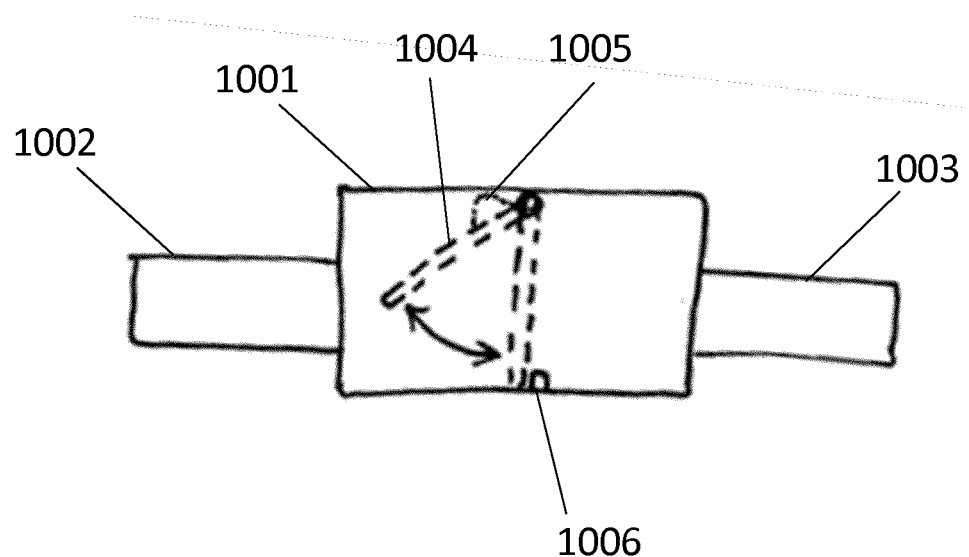

FIGS. 27a and 27b are schematics of a simple one way valve 1000 of this invention. They are configured to open easily to allow flow in one direction, and close quickly and automatically once the direction of the pressure gradient (and hence the direction of flow) across the valve changes. Valve 1000 comprises a body section 1001 with a pair of tube connectors 1002 and 1003 at either end. The body 1001 has a generally square or rectangular section, so that flap 1004 can be hinged at an outer edge and move freely from an open to a closed position. A stop 1005 is provided so that the flap is prevented from reaching a fully open position where a change in flow direction would not cause it to close. A second stop 1006 prevents the flap from moving beyond the fully closed position once the pressure gradient is reversed.

Figure 28A:
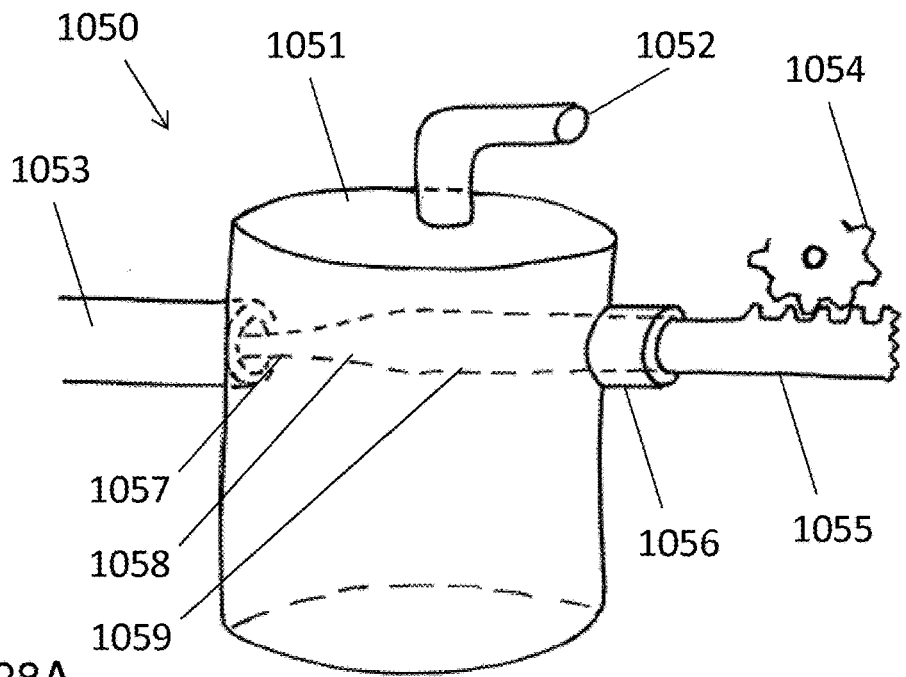
FIG. 28A illustrates a portion of a pulsatile aspiration system of this invention.
Figure 28B:
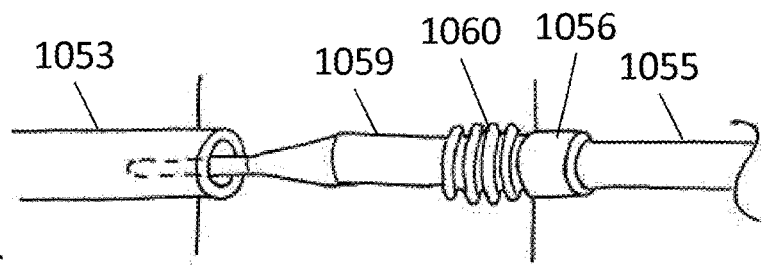
FIGS. 28B-28D illustrate various states of an element of the pulsatile aspiration system of FIG. 28A.
Figure 28C:
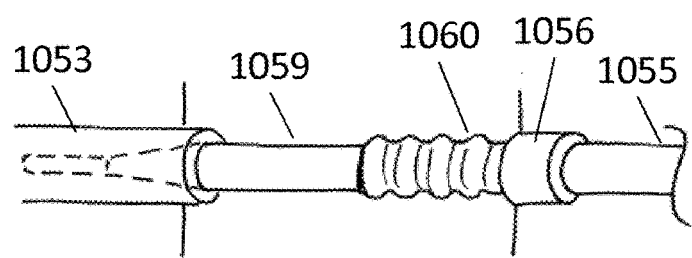
Figure 28D:
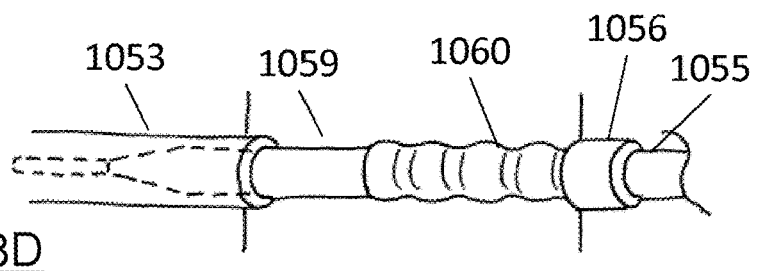

FIG. 28a is a schematic of a portion of a pulsatile pump system 1050 of this invention. Canister 1051 is connected to a vacuum pump (not shown) by connecting tube 1052, and to a treatment catheter (not shown) by connecting tube 1053. In use a vacuum is generated within the canister by the vacuum pump and thus blood and thrombus are aspirated through a treatment catheter and through tube 1053 into the canister. A pulsatile waveform as described in relation to FIG. 24b can be generated by oscillation back and forth of obturator 1055, which is guided through the canister by guide port 1056, and enters the mouth of tube 1053 on the other side of the canister. The obturator can be moved back and forth by a simple gear mechanism as shown or by any of the other means of reciprocation well known in the art. FIGS. 28b-d show the obturator of FIG. 28a in various different positions, and also show a corrugated element 1056 which may be used to ensure that movement of the obturator does not create leakage into the canister.

FIG. 28b (and FIG. 28a) show the obturator in the open position where only the narrow guide portion 1057 is positioned within the mouth of tube 1053. In this position a steady state vacuum may be maintained with little or no restriction from the obturator. FIG. 28c shows the obturator in the closed position where the tapered portion 1058 of the obturator is fully within the mouth of tube 1053. In this position tube 1053 is no longer subject to the vacuum within the canister and the vacuum level within the tube (and connected catheter) will start to decay. The rate of decay of this vacuum can be significantly accelerated by further advancement of the obturator to the position shown in FIG. 28d, which provides a positive displacement to the fluid (or gas) within tube 1053, having a similar effect to the piston and diaphragm movements described in systems 700, 900 and 950.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

What is claimed is:

1. A system for removing an occlusive clot from a blood vessel, the system comprising:
    a catheter comprising a proximal end and a distal end; and
    an apparatus configured to rhythmically deliver a pressure gradient at the distal end of the catheter, the apparatus comprising:
        a vacuum pump;
        a pulse generator located between the vacuum pump and the proximal end of the catheter; and
        a pair of one-way valves positioned on either side of the pulse generator;
    wherein in a first state of the apparatus, the vacuum pump is configured to apply a steady state vacuum level at the proximal end of the catheter, and
    wherein in a second state of the apparatus, a vacuum level applied by the vacuum pump is maintained and the pulse generator produces a pressure differential waveform comprising a sequence of positive and negative pressure pulses between the pair of one-way valves such that at least a portion of the sequence of positive and negative pressure pulses is produced at the catheter distal end.

2. The system of claim 1, wherein the pulse generator is integral or separate with the vacuum pump.

3. The system of claim 2, comprising a flexible tubing between the vacuum pump and the proximal end of the catheter.

4. The system of claim 3, wherein the pulse generator is applied to the flexible tubing, and wherein the steady state vacuum level of the first state is provided in the flexible tubing.

5. The system of claim 3, wherein the pulse generator comprises a reciprocating plunger or a rotatable cam.

6. The system of claim 5, wherein the rotatable cam comprises an outer bearing to minimize drag on the flexible tubing.

7. The system of claim 6, wherein the outer bearing comprises a sliding outer layer.

8. The system of claim 1, comprising a controller for controlling the apparatus for generating a pulsatile vacuum source, and wherein the controller is adapted to vary a pressure over time in a waveform.

9. The system of claim 2, further comprising a canister disposed between the vacuum pump and the pulse generator.

10. A system for removing an occlusive clot from a blood vessel, comprising:
    a catheter for applying a vacuum to the occlusive clot; and
    an apparatus for generating an additional energy to be applied to the occlusive clot, the apparatus comprising a vacuum pump, a pulse generator, and a pair of one-way valves positioned on either side of the pulse generator,
    wherein the apparatus is adapted to apply a variable pressure to pulse the occlusive clot at a distal tip of the catheter,
    in a first state, the vacuum pump applies a steady state vacuum level through the distal tip, and
    in a second state the steady state vacuum level applied by the vacuum pump is maintained and the pulse generator produces a pressure differential waveform comprising a sequence of pressure pulses between the pair of one-way valves such that at least a portion of the sequence of pressure pulses is produced at the catheter distal tip.

11. The system of claim 10, wherein the variable pressure applied by the apparatus is adapted to produce a variable pressure differential between the catheter and a blood pressure around the occlusive clot.

12. The system of claim 10, wherein the variable pressure is adapted to provide additional energy to the occlusive clot to overcome the extrusion energy required to deform and aspirate the occlusive clot.

13. The system of claim 10, wherein applying a variable pressure differential to the occlusive clot is adapted to change a friction between the occlusive clot and the catheter from static to dynamic friction reducing a total friction and facilitating aspiration of the occlusive clot into the catheter.

14. The system of claim 10, wherein applying a variable pressure differential to the occlusive clot is adapted to increase a porosity of the occlusive clot reducing a deformation force required to aspirate the occlusive clot.

15. The system of claim 10, wherein a pressure in the distal tip is always less than a surrounding blood pressure.

16. The system of claim 10, wherein a pressure in the distal tip is always greater than a surrounding blood pressure.

17. The system of claim 10, wherein moving one or more pistons in a fluid chamber in the apparatus generates a pressure waveform with a pressure differential when plotted versus time.

18. The system of claim 17, wherein the one or more pistons are driven by a rotating mechanical drive system, a linear drive system, a piezoelectric system, or a pneumatic cylinder.

19. The system of claim 10, further comprising a canister disposed between the vacuum pump and the pulse generator.

* * * * *